(12) United States Patent
Yasui et al.

(10) Patent No.: US 10,184,948 B2
(45) Date of Patent: *Jan. 22, 2019

(54) AUTOMATED ANALYZER

(71) Applicant: HITACHI HIGH-TECHNOLOGIES CORPORATION, Tokyo (JP)

(72) Inventors: Akihiro Yasui, Tokyo (JP); Yoshihiro Suzuki, Tokyo (JP); Hitoshi Tokieda, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/245,237

(22) Filed: Aug. 24, 2016

(65) Prior Publication Data

US 2016/0363604 A1 Dec. 15, 2016

Related U.S. Application Data

(62) Division of application No. 14/352,192, filed as application No. PCT/JP2012/076377 on Oct. 12, 2012, now Pat. No. 9,442,128.

(30) Foreign Application Priority Data

Oct. 18, 2011 (JP) ................. 2011-228426

(51) Int. Cl.
  *G01N 35/10* (2006.01)
  *G01N 35/00* (2006.01)
  (Continued)

(52) U.S. Cl.
  CPC ....... *G01N 35/0092* (2013.01); *G01N 35/025* (2013.01); *G01N 35/04* (2013.01);
  (Continued)

(58) Field of Classification Search
  CPC ............... G01N 35/0092; G01N 35/1009
  See application file for complete search history.

(56) References Cited

U.S. PATENT DOCUMENTS

2004/0105783 A1 6/2004 Yamazaki et al.
2004/0245275 A1 12/2004 Yanami et al.
(Continued)

FOREIGN PATENT DOCUMENTS

JP 03-140869 A 6/1991
JP 06-082460 A 3/1994
(Continued)

OTHER PUBLICATIONS

Extended European Search Report received in corresponding European Application No. 12841806.8 dated Aug. 17, 2015.

*Primary Examiner* — Kathryn Wright
(74) *Attorney, Agent, or Firm* — Mattingly & Malur, PC

(57) ABSTRACT

An automated analyzer maintains high processing capacity and dispensation accuracy even when items requiring dilution/pretreatment and general reaction measurement are mixed. A plurality of sample dispensing mechanisms are independently driven and each include a sample collection position, a sample nozzle for collecting the sample, and a washing tank for washing the sample nozzle. The sample dispensing mechanisms are configured to collect the sample from a plurality of sample collection positions and are operated independently to perform sample dispensation into reaction containers on a reaction disc. At least one of the sample dispensing mechanisms is provided for each of a sample requiring dilution/pretreatment and a sample that does not require dilution/pretreatment. The automated analyzer is provided with a control means for causing the respective mechanisms to be operated in a dedicated manner. The sample is dispensed such that no vacancy is created in the reaction containers.

7 Claims, 15 Drawing Sheets

1 — Reaction disc  2 — Reaction container  3 — Washing mechanism
4 — Spectrophotometer  5 — Stirring mechanism  6 — Stirring mechanism
7 — Reagent dispensing mechanism  7a — Reagent nozzle
8 — Reagent dispensing mechanism  8a — Reagent nozzle  9 — Reagent disc
10 — Reagent bottle  11 — Sample dispensing mechanism  11a — Sample nozzle
12 — Sample dispensing mechanism  12a — Sample nozzle  13 — Washing tank
14 — Washing tank  15 — Sample container  16 — Rack
17 — Sample transport mechanism  18 — Reagent pump  19 — Sample pump
20 — Washing pump  21 — Controller  30 — Washing tank  31 — Washing tank
32 — Washing tank  33 — Washing tank

(51) Int. Cl.
*G01N 35/02* (2006.01)
*G01N 35/04* (2006.01)

(52) U.S. Cl.
CPC ..... *G01N 35/1002* (2013.01); *G01N 35/1009* (2013.01); *G01N 2035/0094* (2013.01); *G01N 2035/0413* (2013.01); *G01N 2035/0444* (2013.01); *G01N 2035/1032* (2013.01)

(56) References Cited

U.S. PATENT DOCUMENTS

| | | |
|---|---|---|
| 2006/0062692 A1 | 3/2006 | Tokieda et al. |
| 2008/0102528 A1 | 5/2008 | Xu et al. |
| 2009/0137048 A1 | 5/2009 | Yamazaki et al. |
| 2011/0014085 A1 | 1/2011 | Yanami et al. |
| 2012/0039748 A1* | 2/2012 | Mimura ............... G01N 35/025 422/63 |

FOREIGN PATENT DOCUMENTS

| | | | |
|---|---|---|---|
| JP | 08-194004 A | 7/1996 | |
| JP | 11-304797 A | 11/1999 | |
| JP | 2004-279356 A | 10/2004 | |
| JP | 2008-180538 | 8/2008 | |
| JP | 2008-180538 A | 8/2008 | |
| WO | WO-2010106885 A1 * | 9/2010 | ........... G01N 35/025 |

* cited by examiner

FIG. 1

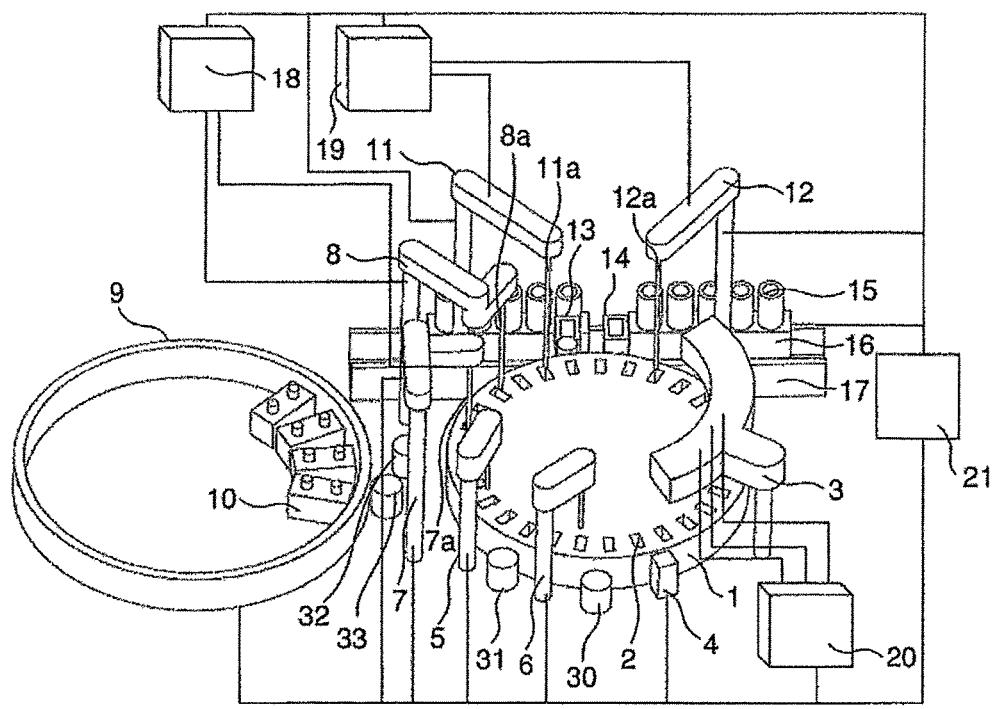

1 ··· Reaction disc   2 ··· Reaction container   3 ··· Washing mechanism
4 ··· Spectrophotometer   5 ··· Stirring mechanism   6 ··· Stirring mechanism
7 ··· Reagent dispensing mechanism   7a ··· Reagent nozzle
8 ··· Reagent dispensing mechanism   8a ··· Reagent nozzle   9 ··· Reagent disc
10 ··· Reagent bottle   11 ··· Sample dispensing mechanism   11a ··· Sample nozzle
12 ··· Sample dispensing mechanism   12a ··· Sample nozzle   13 ··· Washing tank
14 ··· Washing tank   15 ··· Sample container   16 ··· Rack
17 ··· Sample transport mechanism   18 ··· Reagent pump   19 ··· Sample pump
20 ··· Washing pump   21 ··· Controller   30 ··· Washing tank   31 ··· Washing tank
32 ··· Washing tank   33 ··· Washing tank

FIG. 2

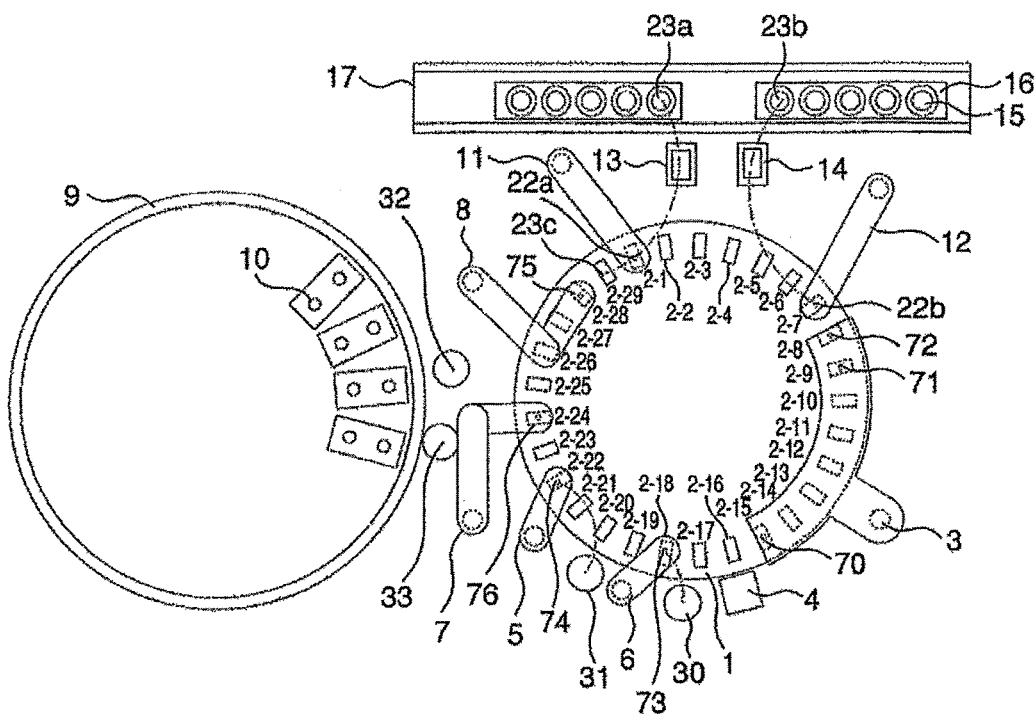

2-1~2-29 ··· Reaction container   22a ··· Sample discharge position
22b ··· Sample discharge position   23a ··· Sample suction position
23b ··· Sample suction position   23c ··· Sample suction position
70 ··· Waste fluid suction position   71 ··· Blank water discharge position
72 ··· Blank water suction position   73 ··· First stirring position
74 ··· Second stirring position   75 ··· Second reagent discharge position
76 ··· First reagent discharge position

24 ··· Sample nozzle   25 ··· Sample nozzle   26 ··· Serum   27 ··· Blood cell

Figure 11:
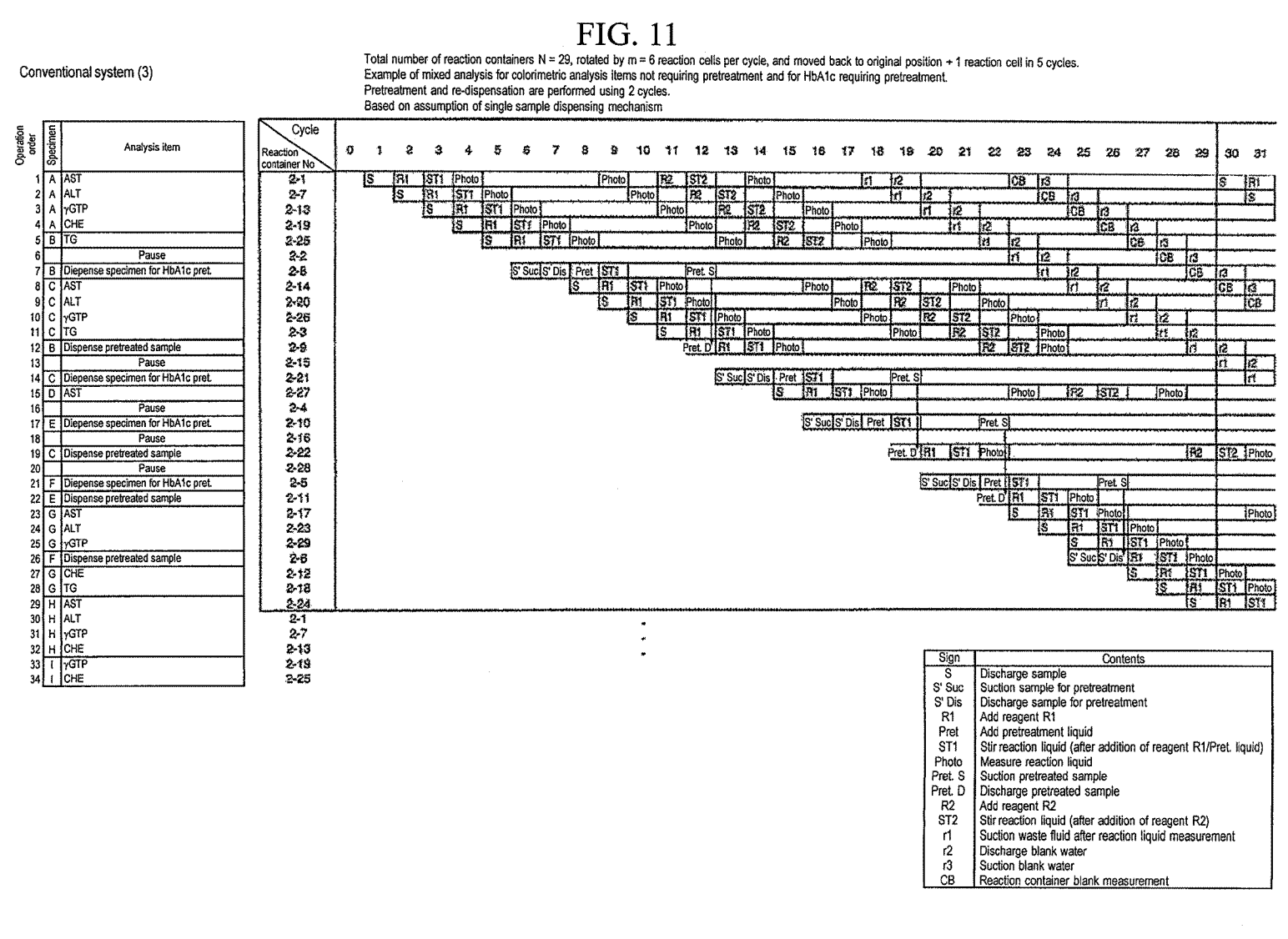

Total number of reaction containers N = 29, rotated by m = 6 reaction cells per cycle, and moved back to original position + 1 reaction cell in 5 cycles.
Example of mixed analysis for colorimetric analysis items not requiring pretreatment and for HbA1c requiring pretreatment.
Pretreatment and re-dispensation are performed using 2 cycles.
Based on assumption of single sample dispensing mechanism.

23d ··· Sample suction position

FIG. 13

28 ⋯ Washing tank    29 ⋯ Washing tank

34 ... Sample dispensing mechanism (θ-θ mechanism)   35 ... Sample dispensing mechanism (X-θ mechanism)
36 ... Sample transport mechanism 1   37 ... Sample transport mechanism 2

AUTOMATED ANALYZER

CROSS REFERENCE TO RELATED APPLICATION

This application is a divisional application of U.S. application Ser. No. 14/352,192, filed Apr. 16, 2014, which is a U.S. national phase application under 35 U.S.C. § 371 of International Application No. PCT/JP2012/076377 filed Oct. 12, 2012, the entirety of the contents and subject matter of all of the above is incorporated herein by reference.

TECHNICAL FIELD

The present invention relates to an automated analyzer that performs quantitative or qualitative analysis of a component of blood, urine, and the like, and particularly to an automated analyzer that handles whole blood and blood cells as a sample.

BACKGROUND ART

An automated analyzer that performs quantitative or qualitative analysis of a specific component contained in a biological sample, such as blood and urine, is indispensable for modern diagnosis due to its analysis result reproducibility, processing speed, and the like. The items for analysis by the automated analyzer are steadily increasing with the progress in medical care. In recent years, there has been a growing demand for an analyzer that can handle hemoglobin A1c analysis to deal with the medical checkup for metabolic syndrome.

A hemoglobin A1c analysis involves analyzing a whole blood or blood cell sample, as opposed to general items for biochemical analysis. Because the whole blood or blood cell sample is hard to analyze as is, pretreatment, such as a hemolysis treatment (whereby red blood cells are ruptured to cause internal components of the blood cells to be eluted), is normally performed. The sample that has been subjected to the hemolysis treatment is analyzed after the addition of a reagent, as in the case of conventional serum samples.

Known methods for implementing the hemolysis treatment in the automated analyzer include a method whereby, as described in Patent Document 1, dispensation control is modified such that the pretreatment can be implemented on a reaction disc, and a method whereby, as described in Patent Document 2, a pretreatment disc (dilute disc) dedicated for implementing the pretreatment is provided.

PRIOR ART DOCUMENTS

Patent Documents

Patent Document 1: JP Patent Publication (Kokai) No. 6-82460 (1994) A
Patent Document 2: JP Patent Publication (Kokai) No. 8-194004 (1996) A

SUMMARY OF THE INVENTION

Problem to be Solved by the Invention

According to the method described in Patent Document 1, a single sample dispensing mechanism is configured to perform, in addition to a dispensing operation for conducting an analysis by adding a reagent to the sample, a dispensing operation for implementing the pretreatment by adding a diluting fluid or a pretreatment fluid to the sample prior to analysis, and to then collect the diluted/pretreated sample from a reaction container and re-dispense the sample into another reaction container. Thus, an automated analyzer with the on-device automatic pretreatment function can be provided without an additional mechanism. However, while the sample dispensing mechanism is carrying out the sample dispensation for pretreatment, the sample dispensation for analysis cannot be performed. As a result, the processing capacity of the apparatus is greatly decreased, particularly when the proportion of analysis items for which the pretreatment is implemented is high.

Further, a plurality of types of samples, such as serum, plasma, whole blood, and blood cells, are dispensed by the single sample dispensing mechanism. These samples have different liquid properties. For example, viscosity (specific viscosity) widely varies depending on the type of sample, such as 1.70 to 2.00 for serum, 1.72 to 2.03 for plasma, 4.40 to 4.74 for whole blood, and 60 or more for blood cells. Thus, when the internal diameter of the nozzle is decreased so as to dispense a minute amount on the order of 1 µL, of serum with high reproducibility, suction resistance is increased in the case of samples with high viscosity, such as whole blood and blood cells. As a result, the settling time of the pressure in the suction pump is increased, which interferes with an accurate and fast sample dispensation.

Conversely, when the nozzle internal diameter is increased so as to accommodate the suctioning of samples with high viscosity, a disadvantage is caused that the dispensation reproducibility is decreased in a dispensation range of minute amounts on the order of 1 µL.

In addition, in a whole blood sample analysis, whole blood is centrifuged to suction blood cells at the bottom of a sample container. Thus, in contrast to the collection of serum or plasma, the nozzle is dipped in the sample for a greater distance, so that case must be exercised with respect to the nozzle washing tank, nozzle shape, and the like. Further, the dispensing operation needs to be modified from when collecting serum or plasma, thus requiring complex control. It is also noted that the method according to Patent Document 2 involves transferring the sample to a dilution table in advance so as to dilute/pretreat the sample, and then analyzing the sample that has been diluted/pretreated in a reaction container.

In the above method, the sample pretreatment is performed on the dilution table in advance. Thus, the sample dispensation from the dilution table to the reaction container can be dedicated for sample analysis. Whole blood and blood cells are also pretreated, so that the viscosity is decreased to the same order as the viscosity of serum. Thus, the viscosity does not interfere with sample dispensation.

However, the addition of the dilution table is associated with an increase in the number of mechanisms, including a diluting container washing mechanism, a stirring mechanism, a diluting pipette for moving the sample from the sample container to the dilution table, a sample suction pump for suctioning the sample with the diluting pipette, and a diluting pipette nozzle washing tank. Thus, an increase in the level of complexity of the mechanisms and an increase in the footprint of the apparatus provide a cause for concern.

Solution to the Problem

In order to achieve the above object, the present invention is configured as follows.

In an automated analyzer that includes a rotatable reaction disc with a plurality of reaction containers arranged in a ring shape, and a measurement unit that measures a mixed liquid of a sample in a sample container and a reagent, a plurality of sample dispensing mechanisms for suctioning a predetermined amount of the sample and discharging a predetermined amount of the suctioned sample are selectively used depending on the type or liquid property of the collected sample. For example, the sample dispensing mechanisms include at least one sample dispensing mechanism that collects a measurement sample such as serum, plasma, or pretreated whole blood, and at least one sample dispensing mechanism that collects a sample for which dilution/pretreatment is implemented before measurement, such as whole blood or blood cells.

The former sample dispensing mechanism (dispensing nozzle) requires one cycle before the sample is suctioned and then discharged. The latter sample dispensing mechanism (dispensing nozzle) requires n times (n is an integer of two or more) the cycle before the sample is suctioned and then discharged. The automated analyzer is further provided with a control unit that exerts control such that, with respect to a reaction container into which the sample is discharged by the latter sample dispensing mechanism, the reaction container is not subjected to sample dispensation by the former sample dispensing mechanism.

The plurality of sample dispensing mechanisms independently include a sample collection position, a sample nozzle for collecting the sample, and a washing tank for washing the sample nozzle, are independently operated, and configured to perform sample dispensation with respect to the reaction containers on the reaction disc.

The automated analyzer is further provided with a sample transport mechanism (transport unit) configured to supply the sample containers to the respective sample collection positions independently. The transport mechanism (transport unit) transports the containers housing the sample that is fed externally of the apparatus.

The sample dispensing mechanisms are generally provided with a nozzle with the tip configured to be placed beneath the liquid level of the sample so as to suction/discharge a predetermined amount of the sample, and with a pressure varying mechanism, such as a syringe, for suctioning the sample into the dipped nozzle by decreasing the pressure within the nozzle. Preferably, a nozzle position moving mechanism may be provided to move the nozzle position so as to enable suction/discharge even when the sample container for housing the sample to be suctioned and the reaction container into which the sample suctioned in the nozzle is discharged are at different positions.

The nozzle position moving mechanism generally includes an arm configured to execute an arc motion about a central axis, with the nozzle attached at the end of the arm. However, this is not a limitation. That a plurality of sample dispensing mechanisms is provided may be paraphrased that there is a plurality of nozzles. For example, when there are four nozzles Nos. 1 to 4, at least two of the nozzles Nos. 1 and 2 are configured to collect only whole blood or blood cells, for which dilution/pretreatment is conducted, from the sample containers disposed at different positions as the sample.

Preferably, when the plurality of sample dispensing mechanisms is used, the mechanisms are configured for X-Y operation, X-θ operation, or provided with a θ-θ mechanism including two rotating axes, so that the operations of the sample dispensing mechanisms do not interfere with each other.

When the sample is suctioned from different positions, adjacent blood collection tubes or a plurality of blood collection tubes spaced apart from each other may be used.

The sample transport mechanism, in the sense that the mechanism can move the sample container position, may be configured to transport a sample disc with a plurality of sample containers circumferentially arranged thereon, or a rack configured to mount one or a plurality of sample containers thereon.

The plurality of sample dispensing mechanisms is configured to be operated independently, and their operation times may not be the same. A sample for measurement that has low viscosity and that does not require much time for collection, such as serum, plasma, or pretreated whole blood, is collected by one sample dispensing mechanism, while a sample that requires time for collection, such as whole blood and blood cells for which dilution/pretreatment is conducted, is suctioned/discharged by another, dedicated sample dispensing mechanism. Thus, sample discharge is conducted in accordance with the vacancy status of the reaction containers on the reaction disc, without an overlap and without creating vacancy in a cell.

The samples suctioned by the respective sample dispensing mechanisms may be discharged into the reaction container at the same position on the reaction disc, or into the reaction containers at different positions on the reaction disc.

Preferably, when the samples are discharged into the reaction containers at different positions on the reaction disc, the reaction container stopped at a position at which the sample is discharged by one sample dispensing mechanism may be controlled to be stopped at a position at which the sample is discharged by the other sample dispensing mechanism in the next cycle or a plurality of cycles later.

Preferably, the sample nozzles of the plurality of sample dispensing mechanisms may have different configurations depending on the type or liquid property of the sample to be suctioned, such as by varying the nozzle internal diameter in accordance with the viscosity of the sample to be collected.

Further preferably, the washing tanks of the plurality of sample dispensing mechanisms may have different configurations, and a configuration for varying the nozzle washing method in accordance with the type of the sample collected by the sample nozzle, and a washing mechanism control means may be provided.

Effects of the Invention

According to the present invention, a decrease in processing capacity due to a wasteful vacancy cycle in the automatic sample dilution/pretreatment step can be prevented.

Because the sample dispensing mechanisms are selectively used depending on the type of sample collected, dispensation accuracy can be increased and maintained regardless of the viscosity and the like of the sample collected.

Further, the only additions to the configuration of the conventional automated analyzer are the sample dispensing mechanisms and associated washing tanks, syringe pumps, and the like. Thus, a high value-added and compact automated analyzer with high per-time processing capacity can be provided.

BRIEF DESCRIPTION OF THE DRAWINGS

FIG. 1 is a perspective view of an implementation example of an automated analyzer to which the present invention is applied.

FIG. 2 is a top view of the implementation example of the automated analyzer to which the present invention is applied.

FIG. 3 illustrates positions at which reaction containers 2 are stopped according to the present application and points at which a spectrophotometer 4 performs measurement according to an implementation example.

FIG. 4 illustrates an example of a cycle chart according to the present application (for analysis of only colorimetric analysis items that do not require pretreatment).

FIG. 5 illustrates an example of a cycle chart according to conventional technology (for analysis of only colorimetric analysis items that do not require pretreatment).

FIG. 8 illustrates an example of the cycle chart according to the present application (for analysis of only HbA1c that requires pretreatment).

FIG. 9 illustrates an example of the cycle chart according to conventional technology (for analysis of only HbA1c that requires pretreatment).

FIG. 10 illustrates an example of the cycle chart according to the present application (where the colorimetric analysis items that do not require pretreatment and the HbA1c analysis that requires pretreatment are mixed).

FIG. 11 illustrates an example of the cycle chart according to conventional technology (where the colorimetric analysis items that do not require pretreatment and the HbA1c analysis that requires pretreatment are mixed).

FIG. 13 illustrates an example of the cycle chart of FIG. 12 according to the present application (for analysis of only HbA1c that requires pretreatment).

MODE FOR CARRYING OUT THE INVENTION

Figure 6:
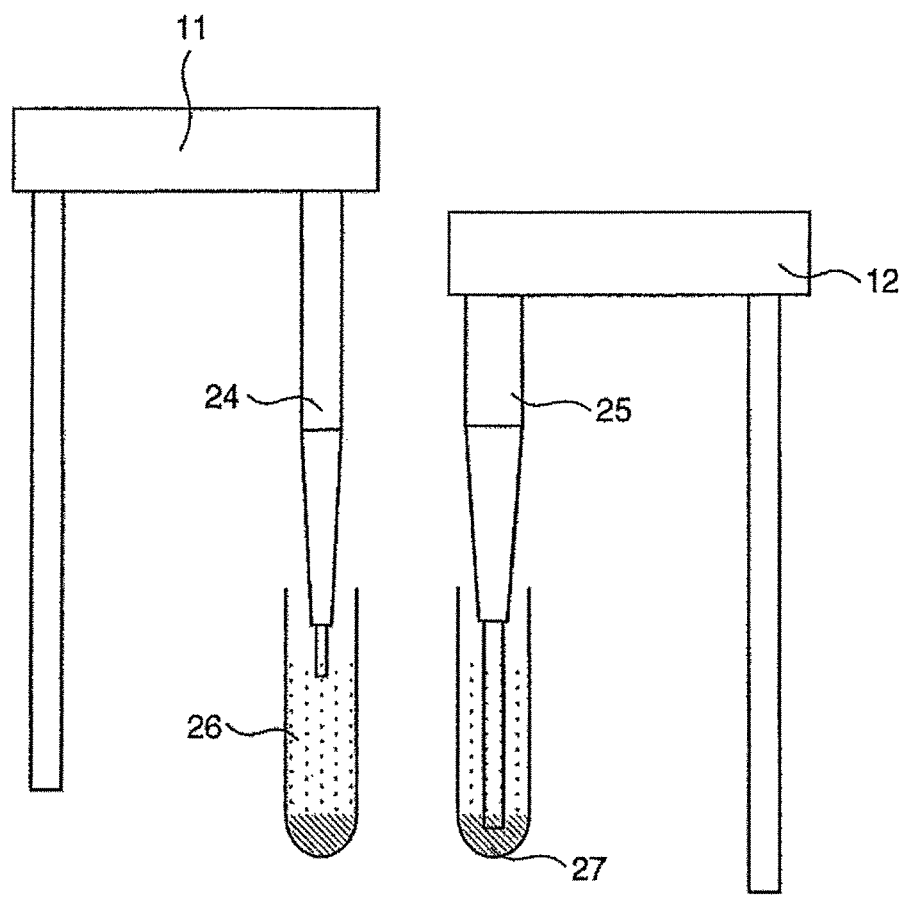
FIG. 6 illustrates an implementation example of selective use of the sample dispensing mechanisms depending on difference in sample collection.

In the following, an embodiment of the present invention will be described with reference to the drawings.

FIGS. 1 and 2 are schematic diagrams illustrating an implementation example of the automated analyzer to which the present invention is applied.

On a reaction disc 1, reaction containers 2 are arranged circumferentially. The reaction disc is controlled to be rotated by a drive mechanism, such as a motor, by a distance corresponding to a predetermined number of the reaction containers in one cycle. In a reagent disc 9, a plurality of reagent bottles 10 can be mounted circumferentially. In the vicinity of the reaction disc 1, a sample transport mechanism 17 for moving a rack 16 on which sample containers 15 are loaded is installed. The transport mechanism has the role of transporting the containers housing samples fed from the outside of the apparatus. Between the reaction disc 1 and the reagent disc 9, reagent dispensing mechanisms 7 and 8 are installed. The reagent dispensing mechanisms 7 and 8 are equipped with reagent nozzles 7a and 8a, respectively. To the nozzles 7a and 8a, a reagent pump 18 is connected. Between the reaction disc 1 and the sample transport mechanism 17, sample dispensing mechanisms 11 and 12 configured to rotate and move up and down are installed. The sample dispensing mechanisms 11 and 12 are equipped with sample nozzles 11a and 12a, respectively. To the sample nozzles 11a and 12a, a sample pump 19 is connected.

The sample nozzles 11a and 12a are moved along an arc about a rotating axis so as to perform sample dispensation from the sample containers to a reaction cell. On the trajectory of the sample nozzle 11a, a sample suction position 23a over the sample transport mechanism, a sample discharge position 22a over the reaction disc, a sample collection position 23c for a diluted/pretreated sample, and a washing tank 13 for washing the sample nozzle are present. On the trajectory of the sample nozzle 12a, a sample suction position 23b over the sample transport mechanism, a sample discharge position 22b over the reaction disc, and a washing tank 14 for washing the sample nozzle are present. The sample nozzles 11a and 12a are disposed such that the trajectories do not interfere with each other. The transport mechanism is controlled by a transport control unit such that the sample container at the sample suction position 23a and the sample container at the sample suction position 23b can be independently controlled and transported. The sample transport mechanism 17 transports the rack 16 from left to right in FIG. 1. The sample suction position 23a is positioned upstream of the transport mechanism 17 with respect to the sample suction position 23b (see FIG. 2).

Around the reaction disc 1, a washing mechanism 3, a spectrophotometer 4, stirring mechanisms 5 and 6, a reagent disc 9, and the sample transport mechanism 17 are disposed. To the washing mechanism 3, a washing pump 20 is connected. Washing tanks 13, 14, 30, 31, 32, and 33 are installed in the operation ranges of the reagent dispensing mechanisms 7 and 8, the sample dispensing mechanisms 11 and 12, and the stirring mechanisms 5 and 6, respectively. Each mechanism is connected to a controller 21 (control unit). The controller 21 (control unit) controls the driving of rotation of the reaction disc, the driving of the sample nozzles, the operations for the suctioning and discharging samples, as well as various mechanisms such as the sample container transport mechanism.

Figure 3:
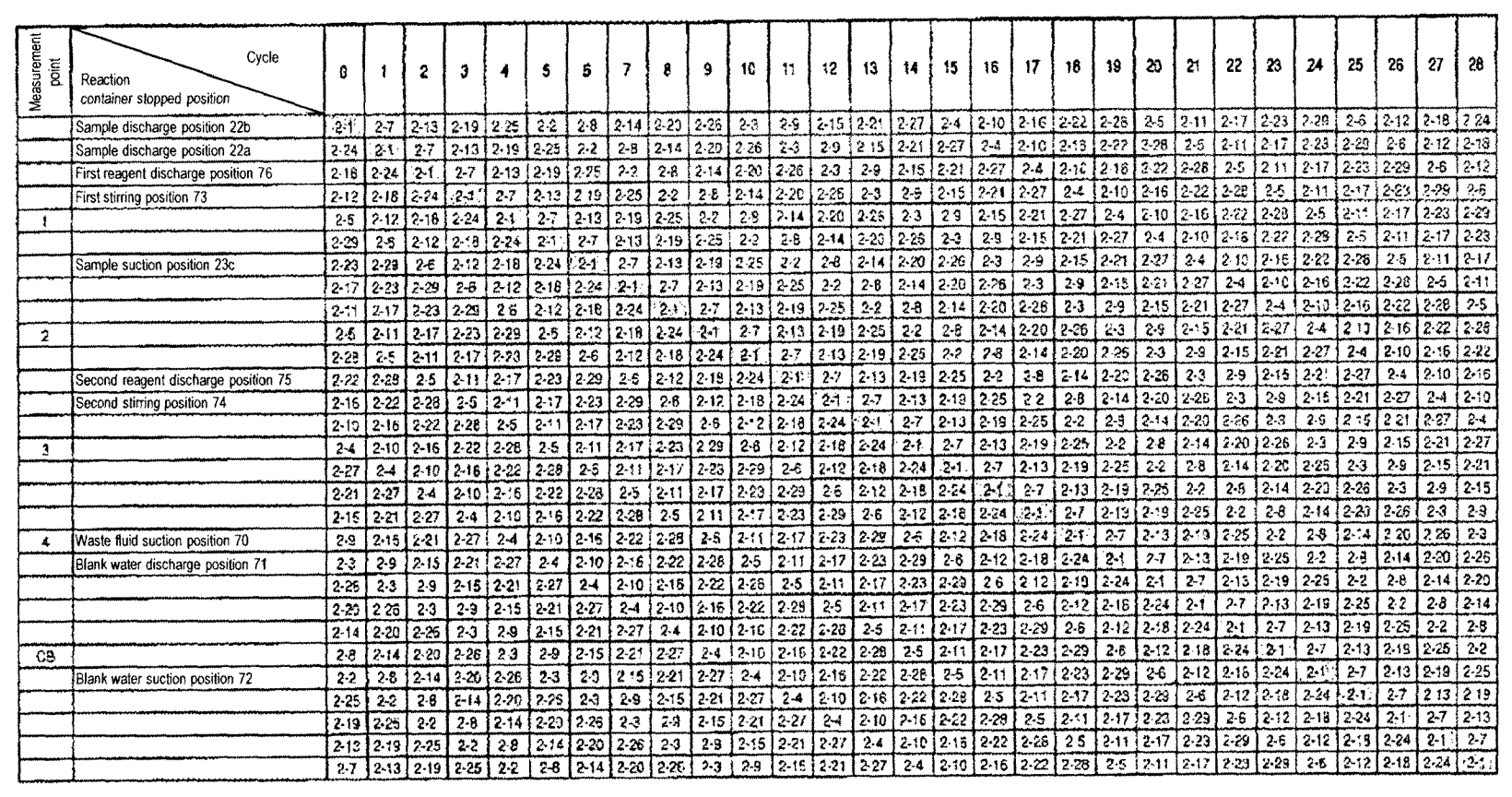

Next, a basic operation of the automated analyzer to which the present invention is applied will be described with reference to FIGS. 2 and 3.

The automated analyzer according to the present implementation example includes 29 reaction containers 2-1 to 2-29 in the reaction disc 1. The reaction disc is repeatedly rotated by as many as six reaction containers in the counterclockwise direction and then stopped in one cycle. Thus, the reaction disc executes a complete revolution plus a rotation by one reaction container in five cycles. By repeating the above operation, the reaction container returns to the same position in 29 cycles. Further, according to the present implementation example, sample collection for analysis items that do not require dilution/pretreatment is performed by the sample dispensing mechanism 11, while collection of a sample for which dilution/pretreatment is conducted prior to analysis is performed by the sample dispensing mechanism 12. The sample dispensing mechanism 11 and the sample dispensing mechanism 12 are provided with dedicated sample discharge positions 22a and 22b, respectively. The sample discharge positions are separated from each other by as many as six reaction containers corresponding to one cycle of rotation of the reaction disc. Thus, the sample dispensing mechanism 12 can discharge a sample into the same reaction container one cycle earlier with respect to the sample dispensing mechanism 11.

FIG. 3 shows stop positions for the reaction containers 2 and points of measurement by the spectrophotometer 4 in the 29 cycles, with cycle 0 corresponding to the time at which the reaction container 2-1 is stopped at the sample discharge position 22b. The movement of the reaction containers 2 will be described with reference to the reaction container 2-1 by way of example.

The reaction container 2-1 that has been at the sample discharge position 22b in cycle 0 is stopped at the sample discharge position 22a in cycle 1. When a sample has been discharged into the reaction container 2-1 by the sample dispensing mechanism 12 in cycle 0, the sample dispensing mechanism 11 discharges no sample into the reaction container 2-1 in cycle 1. In cycle 2, the reaction container 2-1 is stopped at a first reagent discharge position 76. At this position, the reagent dispensing mechanism 7 adds a reagent R1 into a measurement sample that does not require dilution/pretreatment, or a diluting fluid/pretreatment fluid into a sample for which dilution/pretreatment is conducted. In cycle 3, the reaction container 2-1 is stopped at a first stirring position 73 at which the sample in the reaction container 2-1 in the form of a reaction liquid is stirred by the stirring mechanism 6. When the sample in the container 2-1 is a measurement sample that does not require dilution/pretreatment, the absorbance of the reaction liquid is measured each time the reaction liquid is passed in front of the spectrophotometer 4 from cycles 3 to 4 and from cycles 8 to 9.

When the sample in the reaction container 2-1 is a sample for which dilution/pretreatment is conducted, the diluted/pretreated sample is collected by the sample dispensing mechanism 11 when the container is stopped at the sample suction position 23c in cycle 6, and the sample is re-dispensed into the reaction container 2-2 stopped at the sample discharge position 22a. Namely, the reaction disc 1 and the reagent dispensing mechanism 8 function as pretreatment units for conducting pretreatment with respect to a whole blood sample or a blood cell sample, and the sample for which pretreatment has been completed is discharged into the reaction container at the sample discharge position 22a by the sample dispensing mechanism 11.

The diluted/pretreated sample that has been re-dispensed into the reaction container 2-2 is stopped at the first reagent discharge position 76 in cycle 7, at which the reagent R1 for analysis and measurement is added by the reagent dispensing mechanism 7, as in the case of the sample that does not require dilution/pretreatment measurement. (The description of the diluted/pretreated sample in the subsequent stop positions will be omitted as it is similar to the case of the sample that does not require dilution/pretreatment measurement.)

The reaction container 2-1 containing the measurement sample that does not require dilution/pretreatment is stopped at a second reagent discharge position 75 in cycle 11, at which a reagent R2 is added by the reagent dispensing mechanism 8 into the reaction liquid. The reaction container 2-1 is stopped at a second stirring position 74 in cycle 12, at which the reaction liquid is stirred by the stirring mechanism 5. From cycles 13 to 14 and from cycles 17 to 18, the reaction container 2-1 is passed in front of the spectrophotometer 4 to measure the absorbance of the reaction liquid.

In cycle 18, the reaction container 2-1 is stopped at a waste liquid suction position 70 at which the washing mechanism 3 suctions the reaction liquid that has been measured and simultaneously adds a washing fluid. In the next cycle 19, the reaction container 2-1 is stopped at a blank water discharge position 71 at which the washing mechanism 3 suctions the washing fluid and simultaneously discharges blank water for performing blank measurement of the reaction container. From cycles 22 to 23, the reaction container 2-1 is passed in front of the spectrophotometer 4 to measure the absorbance of the reaction liquid. In cycle 24, the reaction container 2-1 is stopped at a blank water suction position 72 at which the washing mechanism 3 suctions the blank water. The cleaned container is reutilized for analysis of a new specimen in step 29 (not shown).

Thus, the basic operation of the automated analyzer according to the present implementation example has been described. In the following, the details of the present invention will be described.

Figure 4:
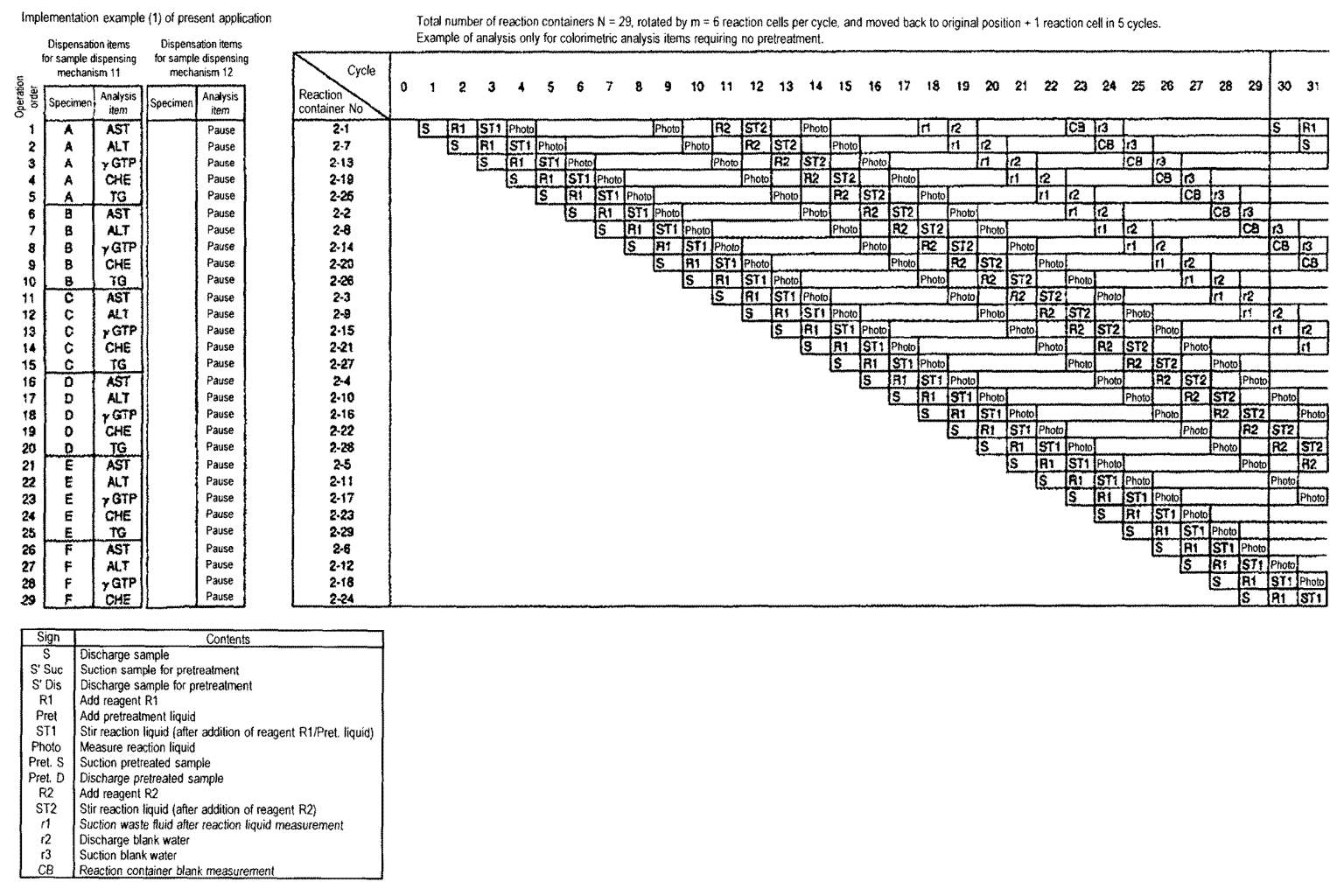

FIG. 4 shows an example of a cycle chart for analyzing only colorimetric analysis items that do not require pretreatment in the automated analyzer to which the present invention is applied. The figure shows the analysis cycle in the horizontal axis, with cycle 0 corresponding to the time at which the reaction container 2-1 is stopped at the sample discharge position 22b. The vertical axis of the figure shows the operation order, the specimens collected by each sample dispensing mechanism, the analysis items requested for the specimens, and the numbers of the reaction containers used for analysis.

The analysis cycle will be described. The sample dispensing mechanism 12 is dedicated for the collection of samples for pretreatment and is not operated in the cycle chart for the present analysis. Thus, nothing is dispensed into the reaction container 2-1 in cycle 0. In cycle 1, the sample dispensing mechanism 11 discharges a sample S for AST analysis of a specimen A into the reaction container 2-1. In cycle 2, simultaneously with the addition of the reagent R1 into the sample S in the reaction container 2-1 by the reagent dispensing mechanism 7, the sample S for ALT analysis of the specimen A is discharged into the reaction container 2-7. In cycle 3, the sample S in the reaction container 2-1, which has been rendered into a reaction liquid, is stirred by the stirring mechanism 6, while simultaneously the reagent R1 is added into the sample S in the reaction container 2-7, and the sample S for γGTP analysis of the specimen A is discharged into the reaction container 2-13. Then, from cycles 3 to 4 and from 8 to 9, the absorbance of the reaction liquid in the reaction container 2-1 is measured by the spectrophotometer 4. In cycles 11 to 12, the reagent R2 is added into the reaction liquid in the reaction container 2-1 by the reagent dispensing mechanism 8, and the reaction liquid is stirred by the stirring mechanism 5. Between cycles 13 and 14 and 17 and 18, the absorbance of the reaction liquid is measured by the spectrophotometer 4. After the measurements for the analysis items are performed by the above cycles, the reaction liquid in the reaction container 2-1 is suctioned up by the washing mechanism 3 in cycle 18, and washing water is injected. The washing water is suctioned up by the washing mechanism 3 in cycle 19, and blank water is added into the cleaned reaction container 2-1. Between cycles 23 and 24, reaction container blank measurement of the reaction container 2-1 is performed by the spectrophotometer 4. In the next cycle 24, the blank water in the reaction container 2-1 is suctioned up by the washing mechanism 3, and the cleaned reaction container 2-1 is reutilized for analysis of a new sample in cycle 30.

Figure 5:
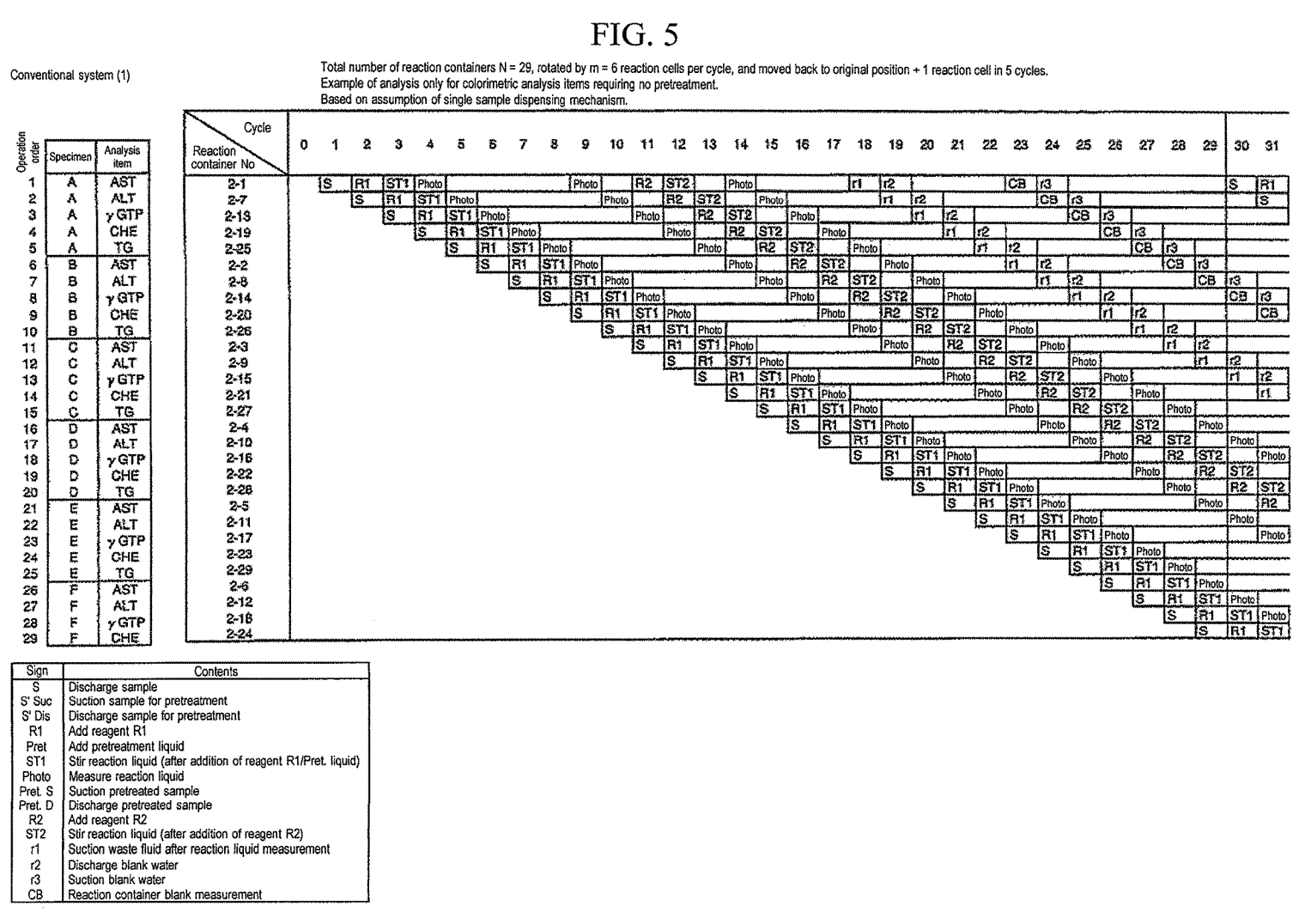

Meanwhile, FIG. 5 shows an example of the cycle chart for analyzing the same analysis items as shown in FIG. 4 by a conventional automated analyzer, such as the one according to Patent Document 1. It is assumed that the conventional automated analyzer does not include the sample dispensing mechanism 12 according to the present implementation example. When cycle 0 corresponds to the time when the reaction container 2-1 is stopped at the sample discharge position 22b, as in FIG. 4, nothing is dispensed into the reaction container 2-1 at cycle 0. Obviously, the cycle chart as shown is similar to the analysis cycle chart of FIG. 4 from cycle 1. Therefore, the description of the details of the subsequent cycles will be omitted.

Thus, there is no difference in processing capacity between the present application and the conventional automated analyzer in terms of analysis of only the colorimetric analysis items that do not require pretreatment. However, in recent years, there have been items that require sample pretreatment in addition to conventional colorimetric items. One example is the hemoglobin A1c (HbA1c) analysis used for a medical checkup for metabolic syndrome. The HbA1c analysis involves analysis of a whole blood sample, in contrast to general biochemical analysis items. Because a whole blood sample is not easily analyzable as is, pretreatment is normally conducted, such as a hemolysis treatment (whereby red blood cells are ruptured to cause internal components of the blood cells to be eluted). Thereafter, a reagent is added to the sample that has been subjected to the hemolysis treatment, as in the case of a normal serum sample, and an analysis is conducted. The present patent is effective when an analysis item that requires advance sample pretreatment, such as HbA1c, is implemented in an automated analyzer with high processing capacity per unit time.

With reference to FIG. 6, an example will be described in which serum suction is performed by the sample dispensing mechanism 11 for analyzing a general biochemical analysis item, and in which whole blood suction is performed by the sample dispensing mechanism 12 for the HbA1c analysis in the automated analyzer according to the present application.

As shown, the sample dispensing mechanism 11 performs sample collection from near the liquid level of serum for an analysis of a general biochemical item. On the other hand, the sample dispensing mechanism 12 needs to collect red blood cells from a blood cell portion (at the bottom of the sample container 15) of a whole blood sample that has been centrifuged for the HbA1c analysis.

Figure 7:
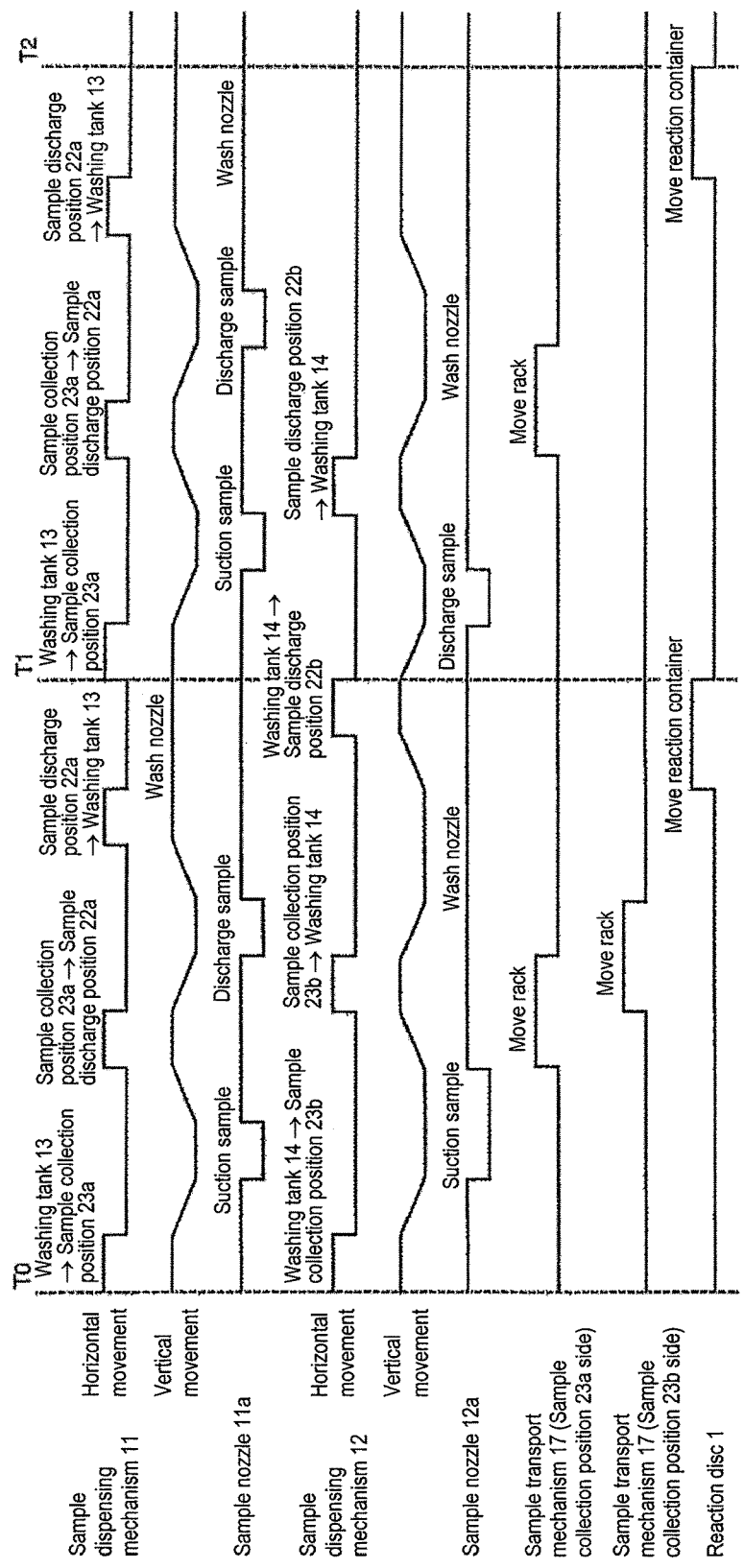
FIG. 7 illustrates an implementation example of a sample dispensing mechanism operation sequence depending on differences in sample collection.

FIG. 7 shows an example of an operation sequence of the automated analyzer equipped with the present invention for dispensing the sample suctioned in FIG. 6 into the reaction containers 2 of the reaction disc 1. The interval between T0 and T1, and the interval between T1 and T2 each correspond to one cycle.

From time T0 to T1, the sample dispensing mechanism 11 is moved to the sample suction position 23a and then moved to the sample discharge position 22a after sample collection. After discharging the sample, the sample dispensing mechanism 11 is moved to the washing tank 13 so as to wash the sample nozzle 11a.

The sample dispensing mechanism 12 is moved to the sample suction position 23b to perform sample collection. When the sample is the centrifuged blood cells shown in FIG. 7, the viscosity is high, so that it takes time before the pressure in the sample nozzle 25 is stabilized after suctioning.

After sample collection, the unwanted serum on the outer periphery of the sample nozzle 25 needs to be washed away in the washing tank 14. After the samples are collected by the sample dispensing mechanisms 11 and 12 and as the sample dispensing mechanisms 11 and 12 begin to be moved horizontally, the sample transport mechanism 17 moves the racks 16 so as to transport new samples to the sample collection positions 23a and 23b (when a plurality of analysis items is not requested for the same sample).

After the samples are discharged by the sample dispensing mechanism 11 and as the sample dispensing mechanism 11 begins to be horizontally moved, the reaction disc 1 moves the reaction containers 2.

From time T1 to T2, the sample dispensing mechanism 11 performs a similar dispensing operation on a new sample.

The sample dispensing mechanism 12 is moved from the washing tank 14 to the sample discharge position 22b. After discharging the sample, the sample dispensing mechanism 12 is returned back to the washing tank 14 to wash the sample nozzle 12a.

Because the sample dispensing mechanism 12 has not yet suctioned the sample at the sample suction position 23b, the sample transport mechanism 17 does not move the rack 16 at the sample collection position 23b. On the other hand, when no other item is requested for the sample at the sample collection position 23a, the rack 16 is moved and a new sample is supplied.

After the samples are discharged by the sample dispensing mechanisms 11 and 12 and as the sample dispensing mechanisms 11 and 12 begin to be horizontally moved, the reaction disc 1 moves the reaction cell. While, in the present example, the sample dispensing mechanism 12 requires twice as many cycles between sample suctioning and sample discharging, the number of times is not limited to two and may be n (n is an integer of two or more). It will be seen that, in the present example, with respect to the reaction container into which no sample was discharged by the sample nozzle 12a but which was rotated (movement of the reaction container in the interval between T0 and T1), a sample is discharged by the sample nozzle 11a (discharging of sample by the sample nozzle 11a in the interval between T1 and T2). From T2 to T3, which is not shown, the present example is controlled such that no sample dispensation (sample discharge) is conducted because the sample container housing the sample discharged by the sample nozzle 12a is at the sample discharge position 22a.

As described above, the sample collection method greatly differs between the serum and the blood cells of whole blood. Thus, independent control is implemented from the supply of samples to the sample collection positions 23a and 23b of the sample transport mechanism 17 to the dispensing operations of the sample dispensing mechanism 11 and the sample dispensing mechanism 12. Accordingly, the respective sample dispensing mechanisms are operated in accordance with the vacancy status of the reaction containers 2 in the reaction disc 1, whereby the processing capacity of the apparatus per unit time can be maximized without creating a vacancy in the reaction containers 2.

As will be seen from FIG. 7, the step of collecting blood cells takes more time than the blood collecting step for serum. In FIG. 7, the operation time of the sample dispensing mechanism 12 is set to take twice as long as the operation time of the sample dispensing mechanism 11. In the conventional automated analyzer as described in Patent Document 1, taking twice as long for the sample collection for HbA1c pretreatment as for the normal sample collection from a serum would create at least one vacancy in the reaction containers 2, which would cause a great decrease in processing capacity.

Further, if the operation time of the sample dispensing mechanism is decreased in order to improve the processing capacity per unit time for the serum sample that does not require dilution/pretreatment, in some cases twice as much time or more may have to be used for the sample collection for HbA1c pretreatment as for serum dispensation. As a result, the number of vacancies in the reaction containers 2 would be increased that much more, causing a further decrease in processing capacity.

In the following, a comparison of an implementation example in which the HbA1c analysis is conducted by the automated analyzer according to the present application and a case in which the HbA1c analysis is conducted by the conventional automated analyzer will be described.

Figure 8:
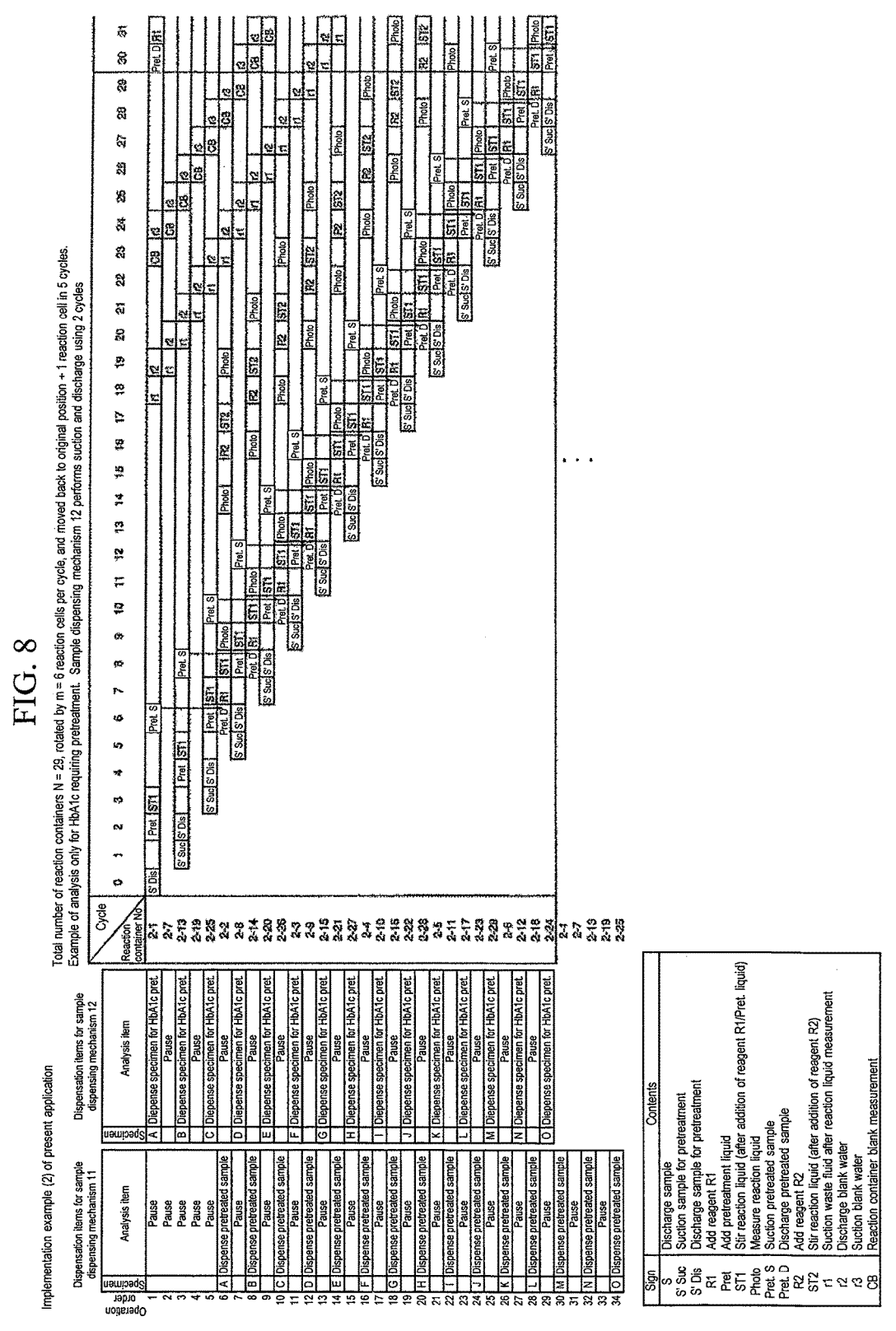

FIG. 8 illustrates an example in which HbA1c measurement is implemented on 15 specimens A to O by the automated analyzer according to the present application. As described above, the sample collection for pretreatment is performed by the sample dispensing mechanism 12, and the re-dispensation of the pretreated sample into the reaction container is performed by the sample dispensing mechanism 11.

In cycle 0, the sample dispensing mechanism 12 discharges a sample S' for pretreatment collected from the specimen A in the previous cycle −1 (not shown) into the reaction container 2-1. Then, in cycle 2, a pretreatment fluid is added to the sample S' in the reaction container 2-1 by the reagent dispensing mechanism 7, while simultaneously the sample S' for pretreatment collected by the sample dispensing mechanism 12 from the specimen B in cycle 1 is discharged into the reaction container 2-13. In cycle 3, the sample in the reaction container 2-1 to which the pretreatment fluid has been added is stirred by the stirring mechanism 6.

In cycle 6, the reaction container 2-1 is stopped at the sample collection position 23c, at which the sample dispensing mechanism 11 collects the pretreated sample from the reaction container 2-1 and re-dispenses the sample into the reaction container 2-2 stopped at the sample discharge position 22a. To the re-dispensed pretreated sample of the specimen A, the reagents R1 and R2 are added, as in the case of the normal sample analysis of the colorimetric items shown in FIG. 4, and then absorbance measurement is conducted by the spectrophotometer 4.

By repeating the above operation, the sample dispensing mechanism 12 continues dispensing of the pretreatment sample without interruptions. In the sixth cycle from the start of dispensing and in subsequent cycles, the sample dispensing mechanism 11 performs the re-dispensing of the pretreated sample every two cycles without interruptions. In 34 cycles from the start of dispensation of the A specimen, the re-dispensation of the O specimen is completed (the cycle chart for the operation order 31 and subsequent orders of is omitted).

Namely, half of the reaction containers with the exception of several reaction containers immediately after the start of sample pretreatment are used for sample pretreatment, while the other half of the reaction containers are used for analysis of the pretreated samples. Thus, no vacancy is created in the reaction containers.

Figure 9:
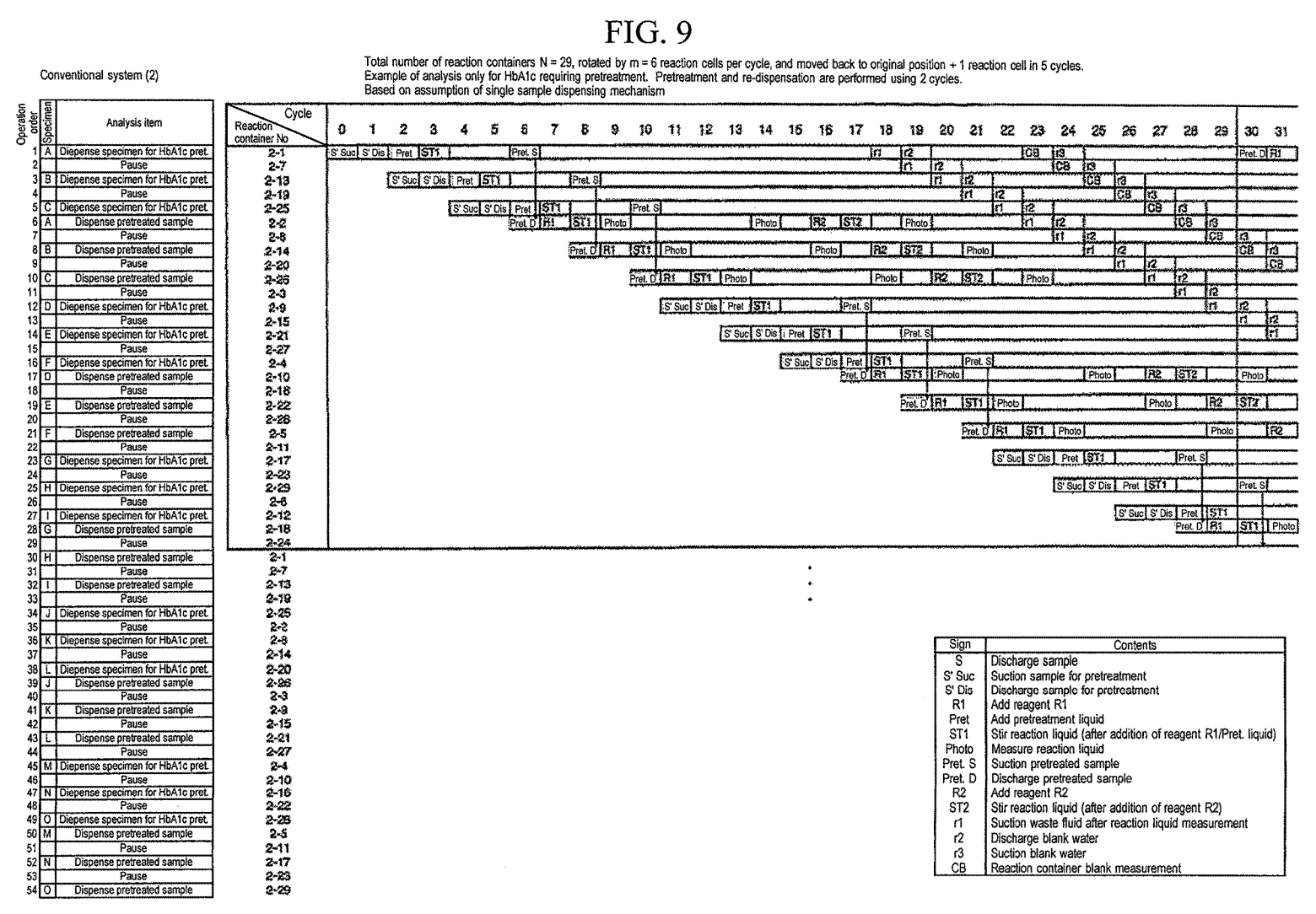

FIG. 9 is an example of implementation of the HbA1c measurement conducted on the 15 specimens A to O by the conventional automated analyzer described in Patent Document 1, as in FIG. 8. It is assumed that the conventional automated analyzer does not include the sample dispensing mechanism 12 according to the present implementation example, as in the case of the description of FIG. 5, and that the sample dispensing mechanism 11 collects the sample for HbA1c pretreatment, collects a pretreated sample from a reaction container 2, and also re-dispenses the sample into another reaction container 2.

The sample dispensing mechanism 11 that has suctioned the sample S' for HbA1c pretreatment from the specimen A stopped at the sample suction position 23a in cycle 0 discharges the sample S' into the reaction container 2-1 stopped at the sample discharge position 22a in cycle 1. In cycle 2, the reagent dispensing mechanism 7 adds the pretreatment fluid into the sample S' in the reaction container 2-1, while simultaneously the sample dispensing mechanism 11 suctions the sample for HbA1c pretreatment from the specimen B. At this time, the reaction container 2-7 stopped at the sample discharge position 22a is not used. In cycle 3, the sample S' in the reaction container 2-1 into which the pretreatment fluid has been added is stirred by the stirring mechanism 6, while simultaneously the sample S' for HbA1c pretreatment from the specimen B is discharged into the reaction container 2-13. Then, in cycle 6, the reaction container 2-1 is stopped at the sample suction position 23c, and the sample dispensing mechanism 11 collects the pretreated sample S' and discharges the sample into the reaction container 2-2 stopped at the sample discharge position 22a. In cycle 7, the reagent dispensing mechanism 7 adds the reagent R1 into the pretreated sample re-dispensed from the reaction container 2-1 into the reaction container 2-2. Thereafter, analysis and measurement are performed until cycle 19. From cycles 23 to 29, washing and blank measurement are performed, and the container is reutilized for the next analysis in cycle 35 (not shown). In cycle 7, the sample dispensing mechanism 11 pauses because the sample dispensing mechanism 11 needs to collect the diluted sample S' placed in the reaction container 2-13 in the next cycle 8, and cannot collect the sample for HbA1c pretreatment which requires two cycles for suction and discharging. Thus, the reaction container 2-8 stopped at the sample discharge position 22a is not used. The reaction liquid in the reaction container 2-1 that has been used for sample pretreatment is suctioned up by the washing mechanism 3 in cycle 18, and washing water is injected. In cycle 19, the washing water is suctioned up by the washing mechanism 3, and blank water is added into the cleaned reaction container 2-1. Between cycles 23 and 24, reaction container blank measurement of the reaction container 2-1 is performed by the spectrophotometer 4. In the next cycle 24, the blank water in the reaction container 2-1 is suctioned up by the washing mechanism 3, and the cleaned reaction container 2-1 is reutilized for the analysis of a new sample in cycle 30.

As described above, in the conventional automated analyzer as described in Patent Document 1, when a plurality of cycles (such as two cycles in the example of FIG. 9) is required for collecting the sample for HbA1c pretreatment, a vacancy is caused in the reaction containers 2 when, as in cycle 2, the sample dispensing mechanism 11 suctions the sample for HbA1c pretreatment, and when, as in cycle 7, the sample dispensing mechanism 11 cannot go to collect the sample for HbA1c pretreatment because the sample dispensing mechanism 11 collects the pretreated sample in the next cycle. As a result, 54 cycles are required from the start of the dispensing for the A specimen to the end of the re-dispensing for the O specimen. Thus, compared with the automated analyzer according to the present application illustrated in FIG. 8, the time for additional 20 cycles is required to process the same number of specimens (the cycle chart for the operation order 30 and the subsequent orders is omitted).

Figure 10:
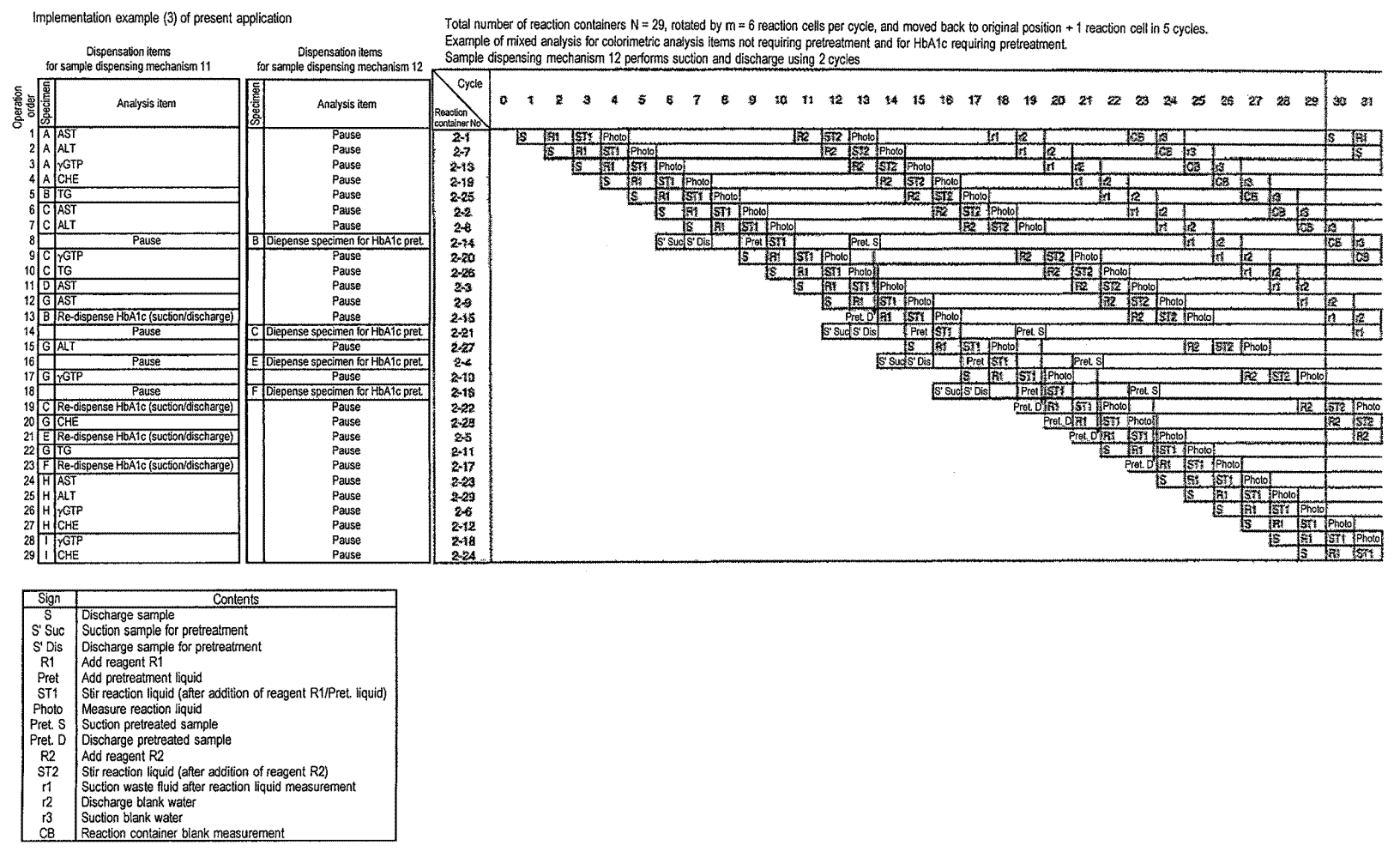

FIG. 10 is an example of implementation of a mixed analysis of nine specimens A to I by the automated analyzer according to the present application for colorimetric analysis items that do not require pretreatment and for HbA1c that requires pretreatment. As described above, the sample collection for pretreatment is performed by the sample dispensing mechanism 12, while the colorimetric analysis items that do not require pretreatment and the re-dispensing of the pretreated sample into the reaction container is performed by the sample dispensing mechanism 11.

When the time at which the reaction container 2-1 is stopped at the sample discharge position 22b is cycle 0, there is no sample to be collected at the sample collection position 23b in cycle 0. Thus, nothing is discharged into the reaction container 2-1. Then, in cycle 1, the sample dispensing mechanism 11 discharges the sample S of the specimen A for AST analysis into the reaction container 2-1. The description of cycle 2 and subsequent cycles is omitted as the analysis operation for the reaction container 2-1 is the same as the cycles described with reference to FIG. 4.

From cycles 1 to 4, samples for AST, ALT, γGTP, and CHE from the A specimen are discharged. In cycle 5, the sample dispensing mechanism 11 discharges the sample S of the specimen B for TG analysis into the reaction container 2-25.

From cycles 5 to 6, the sample transport mechanism 17 moves the sample container 15 containing the specimen B from the sample suction position 23a to the sample suction position 23b, while simultaneously moving the specimen C to the sample suction position 23a. In cycle 6, the sample dispensing mechanism 12 suctions the sample S' of the B specimen for HbA1c pretreatment, while simultaneously the sample dispensing mechanism 11 suctions the sample S of the C specimen for AST analysis, and discharges the sample into the reaction container 2-2. In cycle 7, the sample dispensing mechanism 12 discharges the sample S' of the B specimen for HbA1c pretreatment into the reaction container 2-14, while simultaneously the sample dispensing mechanism 11 suctions the sample S of the C specimen for ALT analysis and discharges the sample into the reaction container 2-8. In cycle 8, because there is no sample at the sample collection position 23b, the sample dispensing mechanism 12 is not operated. In the reaction container 2-14 stopped at the sample dispensation position 22a, the sample S' of the B specimen for HbA1c pretreatment that has been discharged in the previous cycle 7 is placed. Thus, the sample dispensing mechanism 11 pauses.

Next, from cycles 9 to 10, the sample dispensing mechanism 11 discharges samples of the specimen C for γGTP and TG analyses into the respective reaction containers. From cycles 10 to 11, the sample transport mechanism 17 moves the sample container 15 containing the specimen C from the sample suction position 23a to the sample suction position 23b, while simultaneously moving the specimen D to the sample suction position 23a.

In cycle 11, the sample dispensing mechanism 11 suctions the sample S of the D specimen for AST analysis, and discharges the sample into the reaction container 2-3. Meanwhile, the sample dispensing mechanism 12 pauses without suctioning a sample in cycle 11, although the C specimen for HbA1c analysis is placed at the sample suction position 23b. This is due to the fact that, even if the sample S' of the C specimen for HbA1c pretreatment is suctioned in cycle 11, the sample S' of the C specimen for HbA1c pretreatment cannot be discharged because the reaction container 2-15 that is stopped at the sample dispensation position 22b in the next cycle 12 is reserved for the re-dispensing of the pretreated sample of the specimen B by the sample dispensing mechanism 11 in cycle 13.

Form cycles 12 to 17, the sample dispensing mechanism 12 suctions and discharges the sample S' of the specimens C, E, and F for HbA1c pretreatment. On the other hand, the sample dispensing mechanism 11 is planned in advance to re-dispense the pretreated sample of the specimen B in the reaction container 2-14 stopped at the sample suction position 23c into the reaction container 2-15 in cycle 13. In the other cycles 12 and 14 to 17, the sample dispensing mechanism 11 performs a dispensing operation by discharging the sample S of the specimen G so as to fill the reaction containers into which the sample dispensing mechanism 12 did not discharge. Thus, there is a priority order when a sample is discharged into a certain reaction container. Because a sample can be suctioned from a reaction container only when stopped at the sample suction position 23c, the discharging of the sample is given the first priority.

The discharging of the sample from the sample suction position 23b is given the second priority, and the discharging of the sample from the sample suction position 23a is given the third priority. In this way, even when a vacancy is created in the reaction containers by the sample dispensing mechanism 12 requiring two cycles for sample suction and discharge, the vacant reaction cell can be filled by the sample dispensing mechanism 11 that can perform sample suction and discharge in one cycle, as described above. Further, by giving priority to sample analysis on the downstream side of the sample transport mechanism 17 and to rack movement, the movement of the rack from upstream and sample collection by the sample dispensing mechanism 11 can be prevented from being blocked. From cycles 12 to 17, at the sample suction position 23b, the samples are switched from C to E and then to F, while at the sample suction position 23a, the specimen G remains. This is because the sample transport mechanism of the automated analyzer according to the present application can supply the samples to the respective sample suction positions independently.

Namely, the sample dispensing mechanisms 11 and 12 may have samples to suction at the respective sample suction positions. Thus, in order to prevent mixing of the samples, it is preferable to determine the priority order in advance, and the priority order described above is preferable. According to the present implementation example, the example has been described in which suctioning and discharging are controlled by the above priority order. In other words, scheduling as to in what cycle sample suctioning or sample discharging should be conducted is made on the control unit side in view of the priority order. Thus, according to the first priority, when there is a cycle in which a sample to which a reagent has been added for pretreatment is suctioned from the reaction container at the sample suction position 23c and discharged at the sample discharge position 22a; namely, when such a cycle is planned, control is exerted such that the reaction disc is rotated without performing the sample discharge by the sample dispensing mechanism 12 that would have been planned for the previous cycle. Further, according to the second priority, when the sample dispensing mechanism 12 has discharged a sample into a reaction container in a certain cycle, the reaction disc is rotated without discharging a sample into the same reaction container in the cycle in which the reaction container comes to the sample discharge position 22a for the sample dispensing mechanism 11, and, in addition, a sample for pretreatment is added to the same container in the next cycle. Further, according to the third priority as well as the first and the second priorities, when no pretreated sample is re-dispensed into the reaction container at the sample discharge position 22a for the sample dispensing mechanism 11, or a sample for pretreatment is dispensed, a sample such as serum is dispensed. By adopting such a priority order, vacancy in the reaction containers in which no sample is housed can be efficiently prevented.

Thus, as long as there is no interruption in the supply of samples to the sample suction position 23a and the sample suction position 23b, the automated analyzer according to the present application can perform sample pretreatment and analysis and measurement without creating vacancy in the reaction containers 2.

In contrast, FIG. 11 illustrates an example of implementation of the mixed analysis of the nine specimens A to I for colorimetric analysis items that do not require pretreatment and for HbA1c requiring pretreatment, as in FIG. 10, by the conventional automated analyzer as described in Patent Document 1.

Detailed description of the analysis operation will be omitted as it is a combination of the above descriptions made with reference to FIGS. 5 and 9. In cycle 6, the sample S' of the specimen B for HbA1c pretreatment is suctioned, so that the reaction container 2-2 becomes vacant. Also in cycle 18, while the sample at the sample collection position is the sample of the specimen F for HbA1c pretreatment, the pretreated sample S' of the specimen C needs to be re-dispensed in cycle 19. Thus, the reaction container 2-2 is vacant (the cycle chart for the operation order 30 and the subsequent orders is omitted). It is seen that, as a result of such vacancy in the reaction containers 2, the conventional automated analyzer according to Patent Document 1 requires 34 cycles to perform the same dispensing operation that the present application requires 29 cycles to perform, thus requiring 5 more cycles and indicating a decrease in processing capacity.

Figure 12:
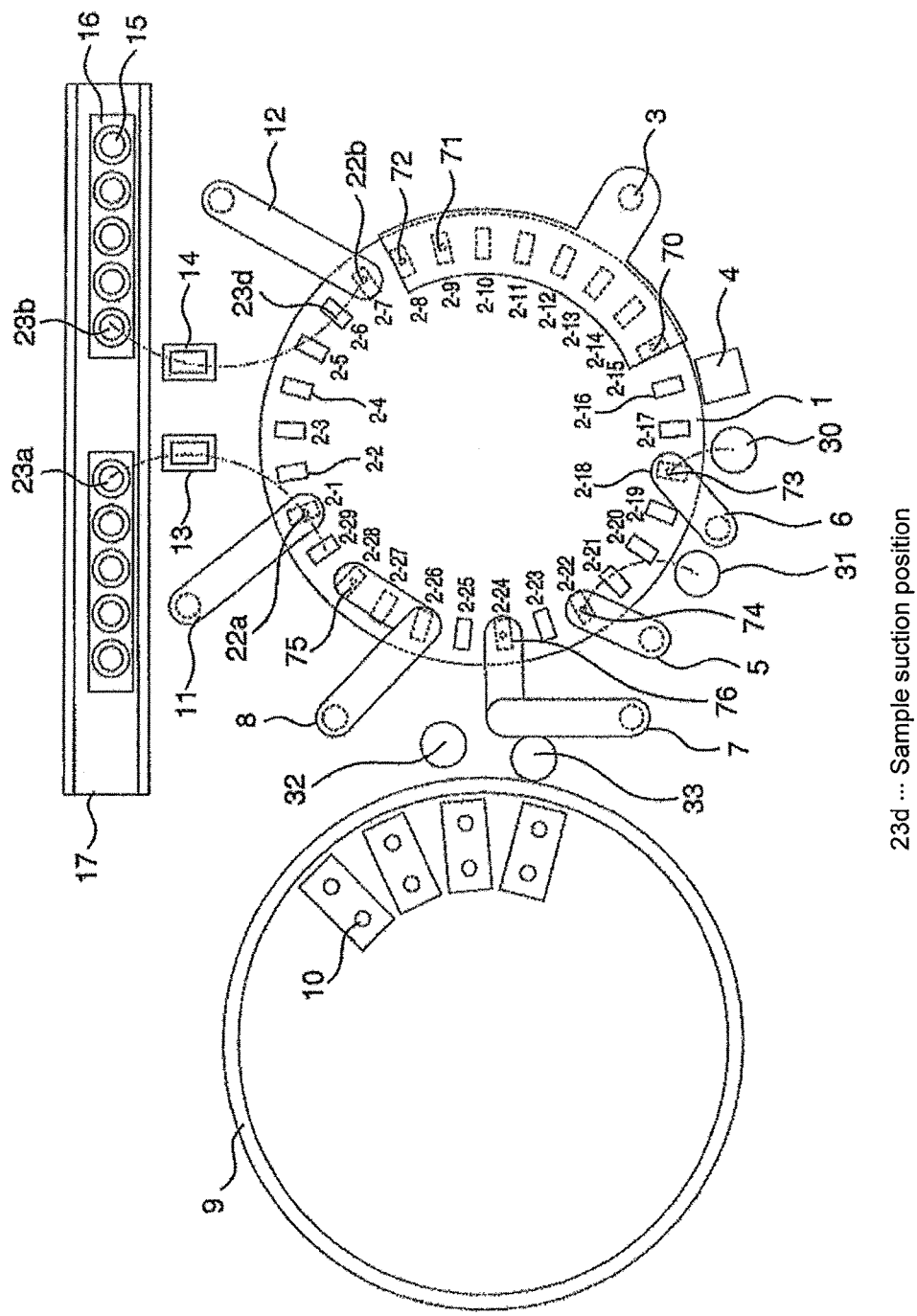
FIG. 12 is a top view of another implementation example of the automated analyzer to which the present invention is applied.
Figure 13:
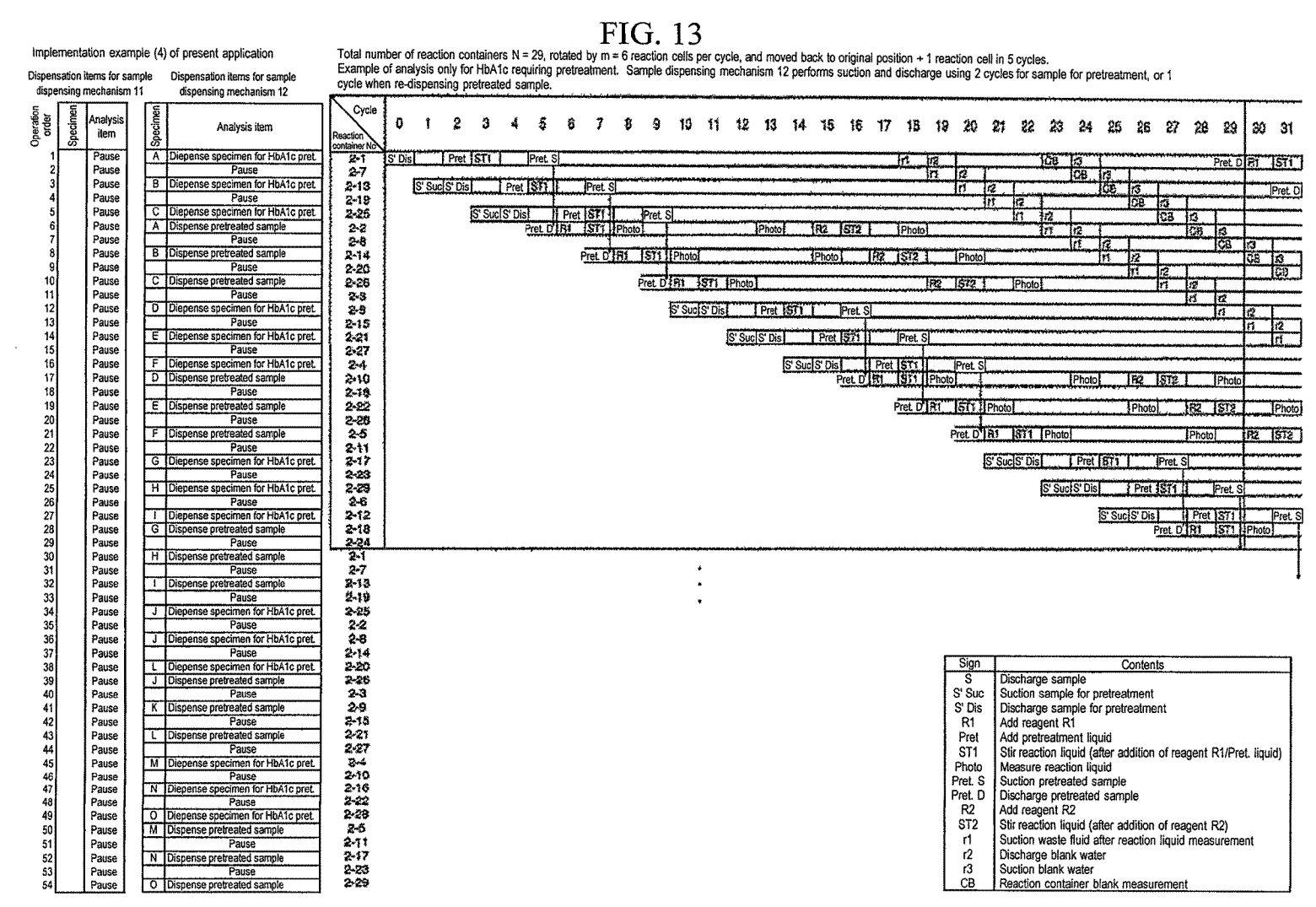

In a selective use of the sample dispensing mechanisms different from the above implementation example, the present application may also adopt a configuration in which the sample suction position 23d for re-dispensing a diluted/pretreated sample is disposed on the trajectory of the sample nozzle 12a of the sample dispensing mechanism 12, as shown in FIG. 12, and in which the items for which no dilution/pretreatment is performed are handled by the sample dispensing mechanism 11 while the items for which dilution/pretreatment is conducted, such as HbA1c, are handled by the sample dispensing mechanism 12. However, in this configuration, as shown in the cycle chart of FIG. 13, the reaction container 2-7 becomes vacant in cycle 1 due to sample suction, or the reaction container 2-8 becomes vacant in cycle 6 in order to wait for a sample for re-dispensation. As a result, the implementation example of FIG. 12 or 13 requires 54 cycles to perform the dispensing operation that the implementation example of FIG. 2 or 8 takes 29 cycles, thus causing a significant decrease in processing capacity. Accordingly, in order to increase the processing capacity per unit time, the selective use of the sample nozzles shown in FIG. 2 is preferable.

Further, as in the example of FIG. 6, according to the present application, the nozzle outer shape or the nozzle internal diameter may be optimized for the selective use of the sample nozzles 24 and 25 between the collection of serum near the liquid level of the sample and the collection of blood cells at the bottom of the sample container 15. For example, the rigidity of the sample nozzle 11a for dispensing serum with relatively low viscosity at high speed is increased, and the internal diameter of the nozzle is decreased so as to enable highly accurate and stable sample dispensation. Conversely, the sample nozzle 12a for dispensing whole blood or blood cells with relatively high viscosity is shaped without protrusions and the like at distances dipped in the sample so as to facilitate washing, and the internal diameter at the tip is increased compared with the sample nozzle 11a. In this way, the suction resistance and the nozzle internal pressure settling time are decreased, whereby the cycle time of the sample dispensing mechanism 12 can be decreased. Accordingly, the internal diameter of the sample nozzle 11a is preferably smaller than the internal diameter of the sample nozzle 12a, and the sample nozzle 11a is preferably controlled so as to decrease the amount by which the nozzle is immersion into the sample.

Figure 14:
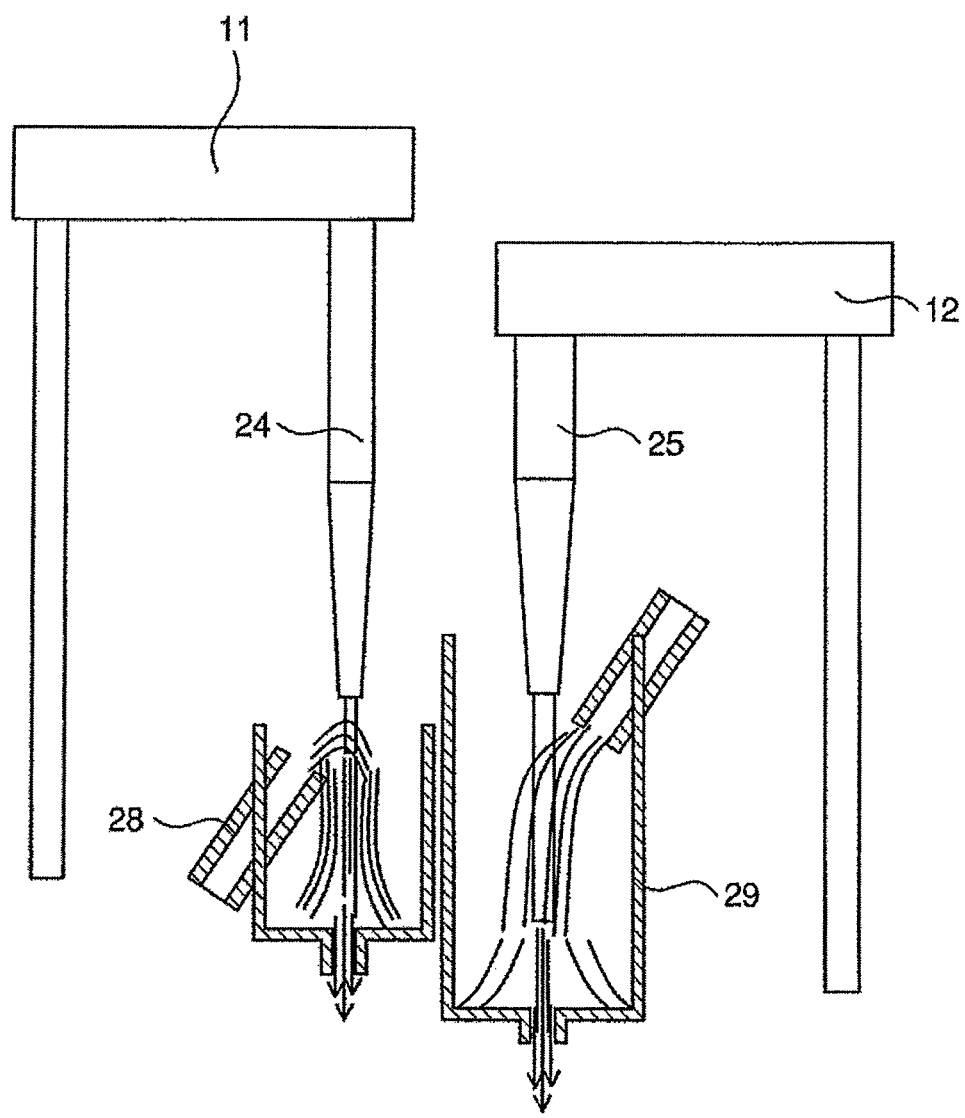
FIG. 14 illustrates an implementation example of the selective use of washing tanks of the automated analyzer to which the present invention is applied.

According to the present application, each sample dispensing mechanism is provided with a washing tank. Thus, as shown in the example of FIG. 14, the configuration of the washing tanks 28 and 29 may be modified to select an optimum shape in accordance with the liquid property of the sample handled by the respective sample nozzles 24 and 25, or the amount of immersion of the nozzles into the sample. In the implementation example of FIG. 14, compared with the washing tank 28 for the sample dispensing mechanism 11 with the sample nozzle 24 with a shorter dip distance (less amount of immersion) with respect to the sample, the washing tank 29 for the sample dispensing mechanism 12 with the sample nozzle 25 with a longer dip distance with respect to the sample is structured such that a long wash distance can be taken. Thus, carry-over is decreased by washing optimization and the wash time is decreased, whereby the cycle time can be decreased. The washing tank 28, as shown, is provided with a washing nozzle configured to eject washing water for washing the outer walls of the sample nozzle 24. The washing tank 29, as shown, is provided with a washing nozzle configured to eject washing water for washing the outer walls of the sample nozzle 25. According to the present application, the amount of immersion of the sample nozzle 25 into the sample is greater than the amount of immersion of the sample nozzle 24. Thus, the area washed by the washing nozzle of the washing tank 29 is greater than the area washed by the washing nozzle of the washing tank 28.

Figure 15:
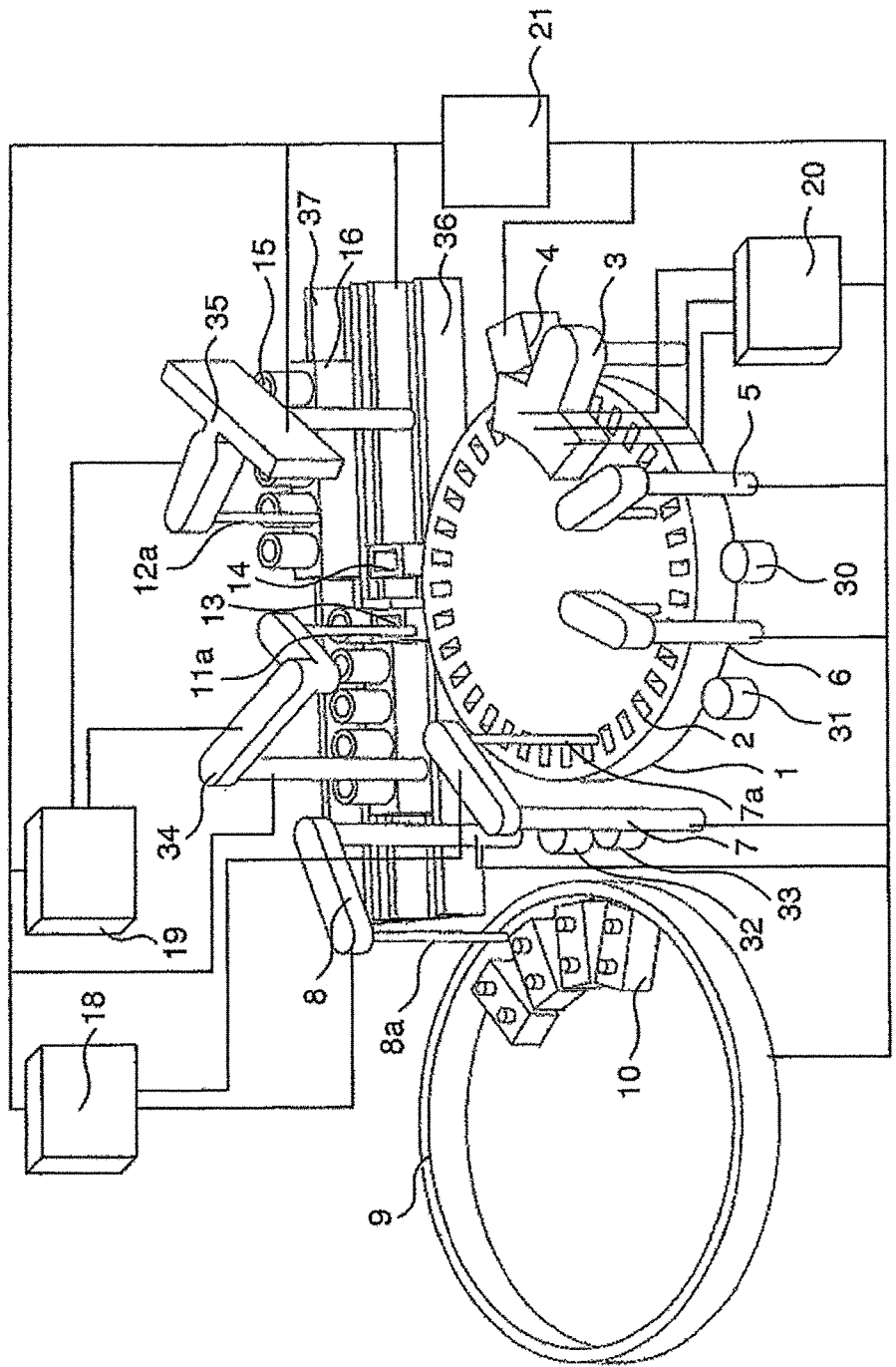
FIG. 15 is a perspective view of another implementation example of the automated analyzer to which the present invention is applied.

FIG. 15 illustrates another implementation example of the automated analyzer to which the present invention is applied. One sample dispensing mechanism 34 is provided with a θ-θ mechanism, and the other sample dispensing mechanism 35 is provided with an X-θ mechanism. The sample dispensing mechanisms are configured such that their operations are not interfered by each other. Depending on the arrangement, either or both of the mechanisms may be combined with a θ rotation mechanism or an X-Y mechanism. When a plurality of sample transport mechanisms 36 and 37 (the number is not limited to two) are provided as the sample transport means, the samples can be supplied to the sample suction positions 23a and 23b independently and more freely.

In the automated analyzer to which the present invention is applied as shown in FIGS. 1 and 2, the sample dispensing mechanism 11 and the sample dispensing mechanism 12 are provided with the dedicated sample discharge positions 22a and 22b, respectively, and the sample discharge positions are separated from each other by as many as six reaction containers corresponding to one cycle of rotation of the reaction disc. The sample dispensing mechanism 12 can discharge a sample into the same reaction container one cycle earlier with respect to the sample dispensing mechanism 11. When it is planned for the sample nozzle 12a of the sample dispensing mechanism 12 to discharge a sample into the reaction container (such as the reaction container 2-7 in FIG. 2) stopped at the sample discharge position 22b, abnormality such as clogging of the nozzle may develop during sample collection, and the sample discharge into the reaction container 2-7 may be cancelled. In this case, information about the abnormality in the sample dispensing mechanism 12 and the cancelling of sample discharge into the reaction container 2-7 is fed back to the sample dispensing mechanism 1. In the next cycle, the reaction disc 1 is rotated in the counterclockwise direction by as much as six reaction containers, and the reaction container 2-7 is moved to the sample discharge position 22a. At this time, the sample dispensing mechanism 1 is fed back with the information about the abnormality in the sample dispensing mechanism 12 and the cancelling of sample discharge into the reaction container 2-7 at least one cycle before the reaction container 2-7 is moved to the sample discharge position 22a. Thus, when the reaction container 2-7 is moved to the sample discharge position 22a and stopped there, the sample dispensing mechanism 1 is controlled to collect the sample from the sample container 15 at the sample suction position 23a and discharge the sample into the reaction container 2-7 stopped at the sample discharge position 22a, so that no vacancy is created in the reaction containers. In this way, the sample dispensing mechanism 11 and the sample dispensing mechanism 12 are provided with the dedicated sample discharge positions 22a and 22b, respectively, and the sample discharge positions are separated from each other by as many as six reaction containers corresponding to one cycle of rotation of the reaction disc, so that by feeding the information about the abnormality in the sample dispensing mechanism 12 back to the sample dispensing mechanism 11, sample dispensation can be continued without creating vacancy in the reaction containers.

Thus, when the sample dispensing mechanism 12 is planned to discharge a sample into which a reagent is added for pretreatment into a reaction container in a certain cycle, and when abnormality is detected in the sample dispensing mechanism 12 in the previous cycle, the sample dispensing mechanism 11, based on the detection of abnormality, can discharge a sample such as serum into the reaction container into which the sample requiring reagent addition for pretreatment was planned to be discharged, in the interval between the cycle planned for reagent addition and the abnormality-detected cycle. For example, in the case of clogging abnormality, the sample dispensing mechanism 12 is provided with a clogging detection mechanism such as a pressure sensor, and information about detection of clogging is transmitted to the control unit so as to control the sample dispensation and discharging by the sample dispensing mechanism 11.

According to the present implementation example, the sample dispensing mechanism 11 and the sample dispensing mechanism 12 are provided with the dedicated sample discharge positions 22a and 22b, respectively, and the sample discharge positions are separated from each other by as many as six reaction containers corresponding to one cycle of rotation of the reaction disc. However, the present invention is not limited to the separation by as many reaction containers as corresponding to one cycle of rotation. Preferably, at least the reaction container at the sample discharge position 22b may reach the sample discharge position 22a within three cycles. Preferably, the sample discharge positions may be separated from each other by as many reaction containers as corresponding to the distance that can be travelled in one cycle of rotation, as according to the present implementation example. This is due to the fact that, as the number of cycles increases, the addition of the reagent for pretreatment into the sample requiring pretreatment is delayed, resulting in an increase in the time before a measurement result is obtained after sample discharge.

According to the present implementation example, the sample discharge position 22a and the sample suction position 23c are adjacent to each other. However, this is not a limitation, and the sample discharge position 22a and the sample suction position 23c may be separated from each other by several reaction containers. Because the relationship of these positions depends on the time required for pretreatment or the size of the reaction disc, the separation of several reaction containers may be provided so as to provide a longer pretreatment time.

Preferably, the sample dispensing mechanism 11 (dispensing nozzle 11a) and the sample dispensing mechanism 12 (dispensing nozzle 12a) may be disposed between the reaction disc and the transport mechanism 17. When a plurality of sample dispensing mechanisms are concentrated in the vacant space, the size of the apparatus can be decreased. Further, the distance of rotation drive of the sample dispensing mechanisms can be decreased, and the distance of movement of the rack 16 can be decreased, whereby throughput can be increased. Preferably, the sample dispensing mechanism 12 may be disposed upstream of the sample dispensing mechanism 11 with respect to the direction of transport of the rack. This is due to the fact that, because the discharge operation by the sample dispensing mechanism 12 is given higher priority than the sample dispensing mechanism 11 according to the above-described priority order, the likelihood of the rack mounting the container to be suctioned being halted at the sample suction position for the sample dispensing mechanism 12 is low, so that the failure to transport a new rack for the sample dispensing mechanism 11 due to congestion of the racks can be prevented.

As described above, according to the present invention, a plurality of sample dispensing mechanisms optimized for the type or liquid property of the samples in the sample containers to be collected, such as serum, plasma, whole blood, blood cells, and urine, is provided. The sample dispensing mechanisms are each provided with a sample collection position, a sample nozzle for collecting the sample, and a washing tank for washing the sample nozzle, and are independently operated to dispense the samples into the reaction containers on the reaction disc. The sample transport mechanism is configured to supply the sample containers to the respective sample collection position independently, whereby a decrease in processing capacity due to a wasteful vacancy cycle in the automatic sample dilution/pretreatment step can be prevented. With respect to the reaction container into which a sample has been discharged by one sample dispensing mechanism, the other sample dispensing mechanism is controlled to perform no sample dispensation, whereby the mixing of samples does not occur. Further, it takes n (n is an integer of 2 or more) cycles before a sample is suctioned by a sample nozzle used for automatic dilution/pretreatment and then discharged. The sample nozzle used for serum and the like discharges a sample into the reaction container into which the sample nozzle for automatic dilution/pretreatment did not discharge a sample and for which the reaction disc was rotated in the n cycles. Thus, a decrease in processing capacity due to a wasteful vacancy cycle can be prevented.

The sample dispensing mechanisms are selectively used depending on the type of the sample to be collected, so that the dispensation accuracy can be increased and maintained regardless of the viscosity and the like of the sample collected.

The only additions to the configuration of the conventional automated analyzer are the sample dispensing mechanisms and the associated washing tanks, syringe pumps, and the like. Thus, a compact and high value-added automated analyzer with high processing capacity per time can be provided.

REFERENCE SIGNS LIST 1 reaction disc
2 reaction container
3 washing mechanism
4 spectrophotometer
5, 6 stirring mechanism
7 reagent dispensing mechanism
7a, 8a reagent nozzle
8 reagent dispensing mechanism
9 reagent disc
10 reagent bottle
11 sample dispensing mechanism
11a, 12a, 24, 25 sample nozzle
12 sample dispensing mechanism
13, 14 washing tank
15 sample container
16 rack
17 sample transport mechanism
18 reagent pump
19 sample pump
20 washing pump
21 controller
22a, 22b sample discharge position
23a, 23b, 23c, 23d sample suction position
26 serum
27 blood cell
30, 31, 32, 33 washing tank
34 sample dispensing mechanism (θ-θ mechanism)
35 sample dispensing mechanism (X-θ mechanism)
36 sample transport mechanism 1
37 sample transport mechanism 2

The invention claimed is:

1. An automated analyzer comprising:
a spectrophotometer configured to measure a reaction in a reaction container of a plurality of reaction containers;
a reaction disc including the plurality of reaction containers on a circumference thereof;
a disc rotation mechanism configured to rotate the reaction disc by a circumferential distance corresponding to a predetermined number of the reaction containers in one cycle, wherein the reaction containers move along the circumference of the reaction disc in the one cycle;
a transport unit configured to transport at least one rack mounting a plurality of sample containers containing at least one liquid,
a first dispensing nozzle configured to suction and discharge liquid from the rack and the reaction containers into the reaction containers at a first discharge position;
a second dispensing nozzle configured to suction and discharge liquid from the rack into the reaction containers at a second discharge position;
a reagent dispensing nozzle configured to discharge a pretreatment reagent into the reaction containers at a third discharge position; and
a controller connected to the disc rotation mechanism, the transport unit, the first dispensing nozzle, the second dispensing nozzle, and the reagent dispensing nozzle,
wherein the controller is configured to:
control the first dispensing nozzle to suction and discharge liquid into a first reaction container within one cycle,
control the second dispensing nozzle such that suction and discharge of liquid into a second reaction container requires n times the one cycle (n is an integer of two or more),
control the first dispensing nozzle to discharge liquid into a third reaction container into which liquid is not discharged by the second dispensing nozzle and which is rotated to the first discharge position within the n times the one cycle,
control the reagent dispensing nozzle to discharge the pretreatment reagent into the second reaction container, and
control the first dispensing nozzle to suction the liquid subjected to reagent pretreatment from the second reaction container, and to discharge the liquid into a fourth reaction container at the first discharge position.

2. The automated analyzer according to claim 1,
wherein the controller is further configured to:
control the disc rotation mechanism to rotate the reaction disc without causing the second dispensing nozzle to discharge liquid into the fourth reaction container in a second cycle before a first cycle in which the fourth reaction container is at the first discharge position.

3. The automated analyzer according to claim 2,
wherein the controller is further configured to:
when liquid is discharged by the second dispensing nozzle into a fifth reaction container at the second discharge position in a third cycle, control the disc rotation mechanism to rotate the reaction disc without causing the first dispensing nozzle to discharge liquid into the fifth reaction container at the first discharge position in a fourth cycle after the third cycle, and
control the reagent dispensing nozzle to discharge the pretreatment reagent into the fifth reaction container in a fifth cycle after the fourth cycle.

4. The automated analyzer according to claim 3, wherein the controller is further configured to:
when an abnormality in the second dispensing nozzle is detected prior to a sixth cycle and when liquid is to be discharged by the second dispensing nozzle into a sixth reaction container at the second discharge position in the sixth cycle, control the first dispensing nozzle to discharge liquid into the sixth reaction container in a seventh cycle.

5. The automated analyzer according to claim 4, wherein:
a serum sample is the liquid discharged by the first dispensing nozzle, and a whole blood or blood cell sample is the liquid discharged by the second dispensing nozzle, and
the first dispensing nozzle and the second dispensing nozzle are disposed between the reaction disc and the transport unit.

6. The automated analyzer according to claim 5, wherein the first discharge position is upstream of the second discharge position with respect to a direction in which the rack is transported by the transport unit.

7. The automated analyzer according to claim 1, wherein the controller is further configured to:
control the disc rotation mechanism to rotate one of the reaction containers at the second discharge position to reach the first discharge position within three cycles.

* * * * *